(12) United States Patent
Slusher et al.

(10) Patent No.: US 11,331,271 B2
(45) Date of Patent: May 17, 2022

(54) BUCCAL, SUBLINGUAL AND INTRANASAL DELIVERY OF FOSPROPOFOL

(71) Applicant: The Johns Hopkins University, Baltimore, MD (US)

(72) Inventors: Barbara Slusher, Kingsville, MD (US); Rana Rais, West Friendship, MD (US); James Vornov, Pikesville, MD (US)

(73) Assignee: The Johns Hopkins University, Baltimore, MD (US)

( * ) Notice: Subject to any disclaimer, the term of this patent is extended or adjusted under 35 U.S.C. 154(b) by 300 days.

(21) Appl. No.: 16/304,800

(22) PCT Filed: May 25, 2017

(86) PCT No.: PCT/US2017/034491
§ 371 (c)(1),
(2) Date: Nov. 27, 2018

(87) PCT Pub. No.: WO2017/205632
PCT Pub. Date: Nov. 30, 2017

(65) Prior Publication Data
US 2020/0289404 A1 Sep. 17, 2020

Related U.S. Application Data

(60) Provisional application No. 62/342,574, filed on May 27, 2016.

(51) Int. Cl.
*A61K 9/00* (2006.01)
*A61K 31/661* (2006.01)
*A61K 9/08* (2006.01)

(52) U.S. Cl.
CPC ............. *A61K 9/008* (2013.01); *A61K 9/006* (2013.01); *A61K 9/0043* (2013.01); *A61K 31/661* (2013.01); *A61K 9/08* (2013.01)

(58) Field of Classification Search
CPC ...... A61K 9/006; A61K 31/661; A61K 9/008; A61K 9/0019; A61K 9/0043; A61K 9/08
See application file for complete search history.

(56) References Cited

U.S. PATENT DOCUMENTS

| 5,288,597 | A | 2/1994 | Hayashi | |
|---|---|---|---|---|
| 5,496,537 | A | 3/1996 | Henry | |
| 6,204,257 | B1* | 3/2001 | Stella | C07K 7/645 514/130 |
| 6,254,853 | B1 | 7/2001 | Hendler et al. | |
| 6,969,508 | B2 | 11/2005 | Dugger, III | |
| 6,977,070 | B2 | 12/2005 | Dugger, III | |
| 8,071,818 | B2* | 12/2011 | Jenkins | C07C 39/06 568/775 |
| 9,327,037 | B2 | 5/2016 | Suk et al. | |
| 2005/0002867 | A1 | 1/2005 | Dugger, III et al. | |
| 2006/0222597 | A1 | 10/2006 | Dugger, III | |
| 2006/0239928 | A1 | 10/2006 | Heit et al. | |
| 2007/0202158 | A1 | 8/2007 | Slusher et al. | |
| 2008/0214508 | A1 | 9/2008 | Slusher et al. | |
| 2009/0075947 | A1 | 3/2009 | Czarnik | |
| 2010/0087536 | A1* | 4/2010 | Xu | A61P 25/00 514/567 |
| 2010/0311698 | A1 | 12/2010 | Patel et al. | |
| 2012/0289470 | A1 | 11/2012 | Heit et al. | |
| 2012/0295866 | A1* | 11/2012 | Shull | C07H 15/18 514/53 |
| 2013/0039864 | A1* | 2/2013 | Ravenelle | A61K 9/1635 424/48 |
| 2015/0257991 | A1* | 9/2015 | Mehta | A61K 31/375 424/59 |

FOREIGN PATENT DOCUMENTS

| CN | 102351895 A | | 2/2012 |
|---|---|---|---|
| WO | 2002013810 A1 | | 2/2002 |
| WO | WO 200213810 A1 | * | 2/2002 |
| WO | 2003059255 A2 | | 7/2003 |
| WO | 2006071995 A1 | | 7/2006 |
| WO | 2009016269 A1 | | 2/2009 |

OTHER PUBLICATIONS

Colombo et al. (ADME-Tox Approaches, Comprehensive Medicinal Chemistry II, 2007). (Year: 2007).*
McCollum, et al., The antiemetic action of propofol. Anaesthesia. Mar. 1988;43(3):239-40.
Krusz, et al., Intravenous propofol: unique effectiveness in treating intractable migraine. Headache. Mar. 2000;40(3):224-30.
Kurt, et al., Anxiolytic-like profile of propofol, a general anesthetic, in the plus-maze test in mice. Pol J Pharmacol. Nov.-Dec. 2003;55(6):973-7.
Velly, et al., Neuroprotective effects of propofol in a model of ischemic cortical cell cultures: role of glutamate and its transporters. Anesthesiology. Aug. 2003;99(2):368-75.
O'Shea, et al., Propofol restores the function of "hyperekplexic" mutant glycine receptors in Xenopus oocytes and mice. J Neurosci. Mar. 3, 2004;24(9):2322-7.
Bennett, et al., Postoperative infections traced to contamination of an intravenous anesthetic, propofol. N Engl J Med. Jul. 20, 1995;333(3):147-54.
Fulton, et al., Propofol. An overview of its pharmacology and a review of its clinical efficacy in intensive care sedation. Drugs. Oct. 1995;50(4):636-57.
Cozanitis, et al., A comparative study of intravenous and rectal administration of propofol in piglets. Acta Anaesthesiol Scand. Oct. 1991;35(7):575-7.

(Continued)

*Primary Examiner* — Blessing M Fubara
(74) *Attorney, Agent, or Firm* — Casimir Jones, S.C.; Jeffrey W. Childers

(57) ABSTRACT

Methods for buccally, sublingually, or intranasally administering a prodrug of propofol to a subject in need of treatment thereof in an amount sufficient to deliver a therapeutically effective amount of propofol to the subject are disclosed.

20 Claims, 17 Drawing Sheets

(13 of 17 Drawing Sheet(s) Filed in Color)

(56) References Cited

OTHER PUBLICATIONS

Berge, et al., Pharmaceutical salts. J Pharm Sci. Jan. 1977;66(1):1-19.

Ceriana, et al., Is rectal administration of propofol effective? Anaesthesia. May 1996;51(5):504.

Choi, et al., Pharmacokinetics of intravenous methotrexate in mutant Nagase analbuminemic rats. Biopharm Drug Dispos. Oct. 2007;28(7):385-92.

Contreras, et al., Bioavailability of Oral Propofol in Humans. ISAP AM 2011. Abstract 20.

Deballi, The use of propofol as an antiemetic. Int Anesthesiol Clin. 2003 Fall;41(4):67-77.

Dong, et al., The actions of propofol on gamma-aminobutyric acid-A and glycine receptors in acutely dissociated spinal dorsal horn neurons of the rat. Anesth Analg. Oct. 2002;95(4):907-14.

Dutta, et al., Emulsion formulation reduces propofol's dose requirements and enhances safety. Anesthesiology. Dec. 1997;87(6):1394-405.

Dutta, et al., Formulation-dependent brain and lung distribution kinetics of propofol in rats. Anesthesiology. Sep. 1998;89(3):678-85.

Fechner, et al., Pharmacokinetics and clinical pharmacodynamics of the new propofol prodrug GPI 15715 in volunteers. Anesthesiology. Aug. 2003;99(2):303-13.

Garnock-Jones, et al., Fospropofol. Drugs. Mar. 5, 2010;70(4):469-77.

Glen, et al., Interaction studies and other investigations of the pharmacology of propofol ('Diprivan'). Postgrad Med J. 1985:61 Suppl 3:7-14.

Hargreaves, et al., A new and sensitive method for measunng thermal nociception m cutaneous hyperalgesia. Pain. Jan. 1988;32(1):77-88.

Hiraoka, et al., Kidneys contribute to the extrahepatic clearance of propofol in humans, but not lungs and brain. Br J Clin Pharmacol. Aug. 2005;60(2):176-182.

Hiraoka, et al., Changes in drug plasma concentrations of an extensively bound and highly extracted drug, propofol, in response to altered plasma binding. Clin Pharmacol Ther. Apr. 2004;75(4):324-30.

Jewett, et al., Propofol and barbiturate depression of spinal nociceptive neurotransmission. Anesthesiology. Dec. 1992;77(6):1148-54.

Kam, et al., Pruritus-itching for a cause and relief? Anaesthesia. Dec. 1996;51(12):1133-1138.

Moghaddam, et al., Plasma pharmacokinetics and tissue distribution of a N-pyrrolo-[1,2-c]imidazolylphenyl sulfonamide in rats. Drug Metab Dispos., Jan. 2002;30(1):47-54.

Mueller, et al., Fospropofol Disodium for Procedural Sedation: Emerging Evidence of Its Value? Clinical Medicine Insights: Therapeutics. Jun. 2010;2:513-522.

Murugaiah, et al., Effects of Intravenous general anesthetics on [3H]GABA release from rat cortical synaptosomes. Anesthesiology. Oct. 1998;89(4):919-28.

Nishiyama, et al., Intrathecal propofol has analgesic effects on inflammation-induced pain in rats. Can J Anaesth. Nov. 2004;51(9):899-904.

Orser, et al., Propofol modulates activation and desensitization of GABAA receptors in cultured murine hippocampal neurons. J Neurosci. Dec. 1994;14(12):7747-60.

Pain, et al., Effect of nonsedative doses of propotol on an innate anxlogenic situation in rats. Anesthesiology. Jan. 1999;90(1):191-6.

Plummer, Improved method for the determination of propofol in blood by high-performance liquid chromatography with fluorescence detection. J Chromatogr. Oct. 9, 1987;421(1):171-6.

Raoof, et al., In vivo assessment of intestinal, hepatic, and pulmonary first pass metabolism of propofol in the rat. Pharm Res. Jun. 1996;13(6):891-5.

Ratnakumari, et al., Effects of propofol on sodium channel-dependent sodium influx and glutamate release in rat cerebrocortical synaptosomes. Anesthesiology. Feb. 1997;86(2):428-39.

Rossi, et al., Effects of environmental enrichment on thermal sensitivity in an operant orofacial pain assay. Behav Brain Res. Mar. 5, 2008;187(2):478-82.

Schywalksy, et al., Pharmacokinetics and pharmacodynamics of the new propofol prodrug GPI 15715 in rats. Eur J Anaesthesiol. Mar. 2003;20(3):182-90.

Sheridan, et al., Low-dose propofol for the abortive treatment of pediatric migraine in the emergency department. Pediatr Emerg Care. Dec. 2012;28(12):1293-6.

Shimizu, et al., Propofol enhances GABA(A) receptor-mediated presynaptic inhibition in human spinal cord. Neuroreport. Mar. 4, 2002;13(3):357-60.

Skrajnar, et al., Effect of replacement fluids saline, gelofusine, and blood on biochemical and hematological parameters in rats subjected to repeated blood sampling. Med Sci Monit. Oct. 2009;15(10):BR293-300.

Soleimanpour, et al., Effectiveness of intravenous dexamethasone versus propofol for pain relief in the migraine headache: a prospective double blind randomized clinical trial. BMC Neurol. Sep. 29, 2012:12:114.

Soleimanpour, et al., Improvement of refractory migraine headache by propofol: case series. Int J Emerg Med. 2012;5:19.

Tall, Housing supplementation decreases the magnitude of inflammation-induced nociception in rats. Behavioral Brain Research. Jan. 2009;197(1):230-233.

Tibbs, et al., HCN1 Channels as Targets for Anesthetic and Nonanesthetic Propofol Analogs in the Amelioration of Mechanical and Thermal Hyperalgesia in a Mouse Model of Neuropathic Pain. J Pharmacol Exp Ther. Jun. 2013;345(3):363-373.

Tsagogiorgas, et al., Buccal absorption of propofol when dosed in 1-perfluorobutylpentane to anaesthetised and conscious Wistar rats and Gottingen mini-pigs. Eur J Pharm Biopharm. Nov. 2013;85(3 Pt B):1310-6.

Unlugenc, et al., Comparative study of the antiemetic efficacy of ondansetron, propofol and midazolam in the early postoperative period. Eur J Anaesthesiol. 2004;21(1):60-65.

Vasileiou, et al., Propofol: a review of its non-anaesthetic effects. Eur J Pharmacol. Mar. 1, 2009;605(1-3):1-8.

Vornov, et al., Pharmacokinetics and Pharmacodynamics of the Glutamate Carboxypeptidase II Inhibitor 2-MPPA Show Prolonged Alleviation of Neuropathic Pain through an Indirect Mechanism. J Pharmacol Exp Ther. Sep. 2013;346(3):406-413.

Welliver, et al., New drug, fospropofol disodium, a propofol prodrug. AANA J. Aug. 2009;77(4):301-8.

Zacny, et al., Propofol at conscious sedation doses produces mild analgesia to cold pressor-induced pain in healthy volunteers. J Clin Anesth. Sep. 1996;8(6):469-74.

Jarineshin, et al., Seizure Duration and Hemodynamic State During Electroconvulsive Therapy: Sodium Thiopental Versus Propofol. Glob J Health Sci. Feb. 2016;8(2):126-131.

Celik, et al., Is infusion of subhypnotic propofol as effective as dexamethasone in prevention of postoperative nausea and vomiting related to laparoscopic cholecystectomy? BioMed Research International. 2015. 249806.

Kumpulainen, et al., Synthesis, in vitro and in vivo characterization of novel ethyl dioxy phosphate prodrug of propofol. Eur J Pharm Sci. Jul. 3, 2008;34(2-3):110-7.

\* cited by examiner

BUCCAL, SUBLINGUAL AND INTRANASAL DELIVERY OF FOSPROPOFOL

CROSS-REFERENCE TO RELATED APPLICATIONS

This application is a 35 U.S.C. § 371 National Stage Entry of International Application No. PCT/US2017/034491 having an international filing date of May 25, 2017, which claims the benefit of U.S. Provisional Application No. 62/342,574 filed May 27, 2016, the contents of which are incorporated herein by reference in their entirety.

BACKGROUND

Propofol (2,6-diisopropylphenol) is a low molecular weight phenol derivative that is widely used as a hypnotic or sedative agent for intravenous administration in the induction and maintenance of anesthesia or sedation in humans and animals. Among its useful characteristics as an anesthetic drug are administration via the intravenous route, rapid onset and offset of anesthesia, rapid clearance, and a side-effect profile that makes it preferable to other injectable anesthetics, such as barbiturates. Additional clinical uses for propofol, including, but not limited to, treatment of migraine, nausea, pain and anxiety, have been proposed (Vasileiou, 2009).

In addition to its sedative and anesthetic effects, propofol has a range of other biological and medical applications. For example, it has been reported to be an anti-emetic, McCollum J S C et al., Anesthesia 43 (1988) 239, an anti-epileptic, Chilvers C R, Laurie P S, Anesthesia 45 (1990) 995, and an anti-pruritic, Borgeat et al., Anesthesiology 76 (1992) 510. See also, Vasileiou, 2009 (proposing additional clinical uses for propofol, including, but not limited to, treatment of migraine, nausea, pain and anxiety).

Anti-emetic and anti-pruritic effects are typically observed at subhypnotic doses, i.e., at doses that achieve propofol plasma concentrations lower than those required for sedation or anesthesia. Antiepileptic activity, on the other hand, is observed over a wider range of plasma concentrations. Borgeat et al., Anesthesiology 80 (1994) 642. Short-term intravenous administration of subanesthetic doses of propofol also has been reported to be remarkably effective in the treatment of intractable migraine and nonmigrainous headache. Krusz J C, et al., Headache, 40 (2000) 224-230. It has further been speculated that propofol may be useful as an anxiolytic, Kurt et al., Pol. J. Pharmacol. 55 (2003) 973-7, neuroprotectant, Velly et al., Anesthesiology 99 (2003) 368-75, muscle relaxant, O'Shea et al., J. Neurosci. 24 (2004) 2322-7, and, due to its antioxidant properties in biological systems, may further be useful in the treatment of inflammatory conditions, especially inflammatory conditions with a respiratory component, and in the treatment of neuronal damage related to neurodegeneration or trauma. Such conditions are believed to be associated with the generation of reactive oxygen species and therefore amenable to treatment with antioxidants. See, e.g., U.S. Pat. No. 6,254,853 to Hendler et al.

Propofol typically is formulated for clinical use as a oil-in-water emulsion. The formulation has a limited shelf-life and has been shown to be sensitive to bacterial or fungal contamination, which has led to instances of postsurgical infections. Bennett S N et al., N Engl J Med 333 (1995) 147. Due to the dense, white color of the formulation, bacterial or fungal contamination cannot be detected by visual inspection of the vial in the first instance.

Not only is propofol poorly water soluble, but it also causes pain at the injection site, which must often be alleviated by using a local anesthetic. Dolin S J, Drugs and pharmacology. In: N. Padfield, Ed., Total Intravenous Anaesthesia. Butterworth Heinemann, Oxford 2000. Due to its formulation in a lipid emulsion, its intravenous administration also is associated with undesirable hypertriglyceridemia in patients, especially in patients receiving prolonged infusions. Fulton B and Sorkin E M, Drugs 50 (1995) 636. Its formulation as a lipid emulsion further makes it difficult to co-administer other IV drugs. Any physical changes to the formulation, such as a change in lipid droplet size, can lead to changes in the pharmacological properties of the drug and cause side effects, such as lung embolisms.

It has further been reported that the use of propofol in anesthesia induction is associated with a significant incidence of apnea, which appears to be dependent on dose, rate of injection, and premedication. Reyes, J G, Glass, P S A, Lubarsky D A, Nonbarbiturate intravenous anesthetics. In: R. D. Miller et al., Eds, Anesthesia. 5.sup.th Ed. Churchill Livingstone, Pa., 2000. Respiratory consequences of administering anesthetic induction doses of propofol, including a reduction in tidal volume and apnea, occur in up to 83% of patients. Bryson et al., Drugs 50 (1995) at 520. Induction doses of propofol also are known to have a marked hypotensive effect, which is dose- and plasma concentration-dependent [Reyes et al., supra]. The hypotension associated with peak plasma levels after rapid bolus injection of propofol sometimes requires the use of controlled infusion pumps or the breaking-up of the induction bolus dose into several smaller incremental doses. Further, the short duration of unconsciousness caused by bolus induction doses renders propofol suitable for only brief medical procedures. For all the above reasons, propofol for induction and/or maintenance of anesthesia must normally be administered in an in-patient setting under the supervision of an anesthesiologist, and is often considered inappropriate for use by non-anesthesiologists in an ambulatory or day case setting.

In addition to its use in induction and maintenance of anesthesia, propofol has been used successfully as a sedative to accompany either local or regional anesthesia in conscious patients. Its sedative properties also have been exploited in diagnostic procedures that have an unsettling effect on conscious patients, such as colonoscopy or imaging procedures. Propofol also has been used as a sedative in children undergoing diagnostic imaging procedures or radiotherapy. A recent development is that of patient-controlled sedation with propofol. This technique is preferred by patients and is as effective as anesthesiologist-administered sedation.

Compared with the widely used sedative midazolam or other such agents, propofol provided similar or better sedative effects when the quality of sedation and/or the amount of time that patients were at adequate levels of sedation were measured. See Fulton B and Sorkin E M, Drugs 50 (1995) 636. The faster recovery and similar or less amnesia associated with propofol makes it an attractive alternative to other sedatives, particularly for patients requiring only short sedation. However, because of the potential for hyperlipidemia associated with the current propofol formulation, and the development of tolerance to its sedative effects, the usefulness of propofol for patients requiring longer sedation is less well established.

Due to its very low oral bioavailability, propofol in its commercially available formulations is generally recognized as not suitable for other than parenteral administration, and must generally be injected or infused intravenously. While propofol is administered intravenously in a clinical setting, it has been suggested that it could be delivered for certain indications via other non-oral routes, such as via inhalation using a nebulizer, transmucosally through the epithelia of the upper alimentary tract, or rectally in the form of a suppository. See, e.g. Cozanitis, D. A., et al., Acta Anaesthesiol. Scand. 35 (1991) 575-7; see also U.S. Pat. Nos. 5,496,537 and 5,288,597]. However, the poor bioavailability of propofol when administered by any other than the intravenous route has hampered the development of such treatments.

SUMMARY

In some aspects, the presently disclosed subject matter provides a method for buccally, sublingually, or intranasally administering a prodrug of propofol, or a pharmaceutically acceptable salt thereof, to a subject in need of treatment thereof in an amount sufficient to deliver a therapeutically effective amount of propofol to the subject.

In other aspects, the prodrug of propofol is a compound of Formula (I):

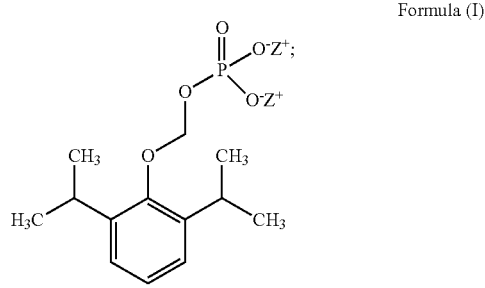

Formula (I)

wherein each Z is independently selected from the group consisting of hydrogen, an alkali metal, and an amine. In particular aspects, the alkali metal is sodium.

In yet more particular aspects, the prodrug of propofol is administered intranasally in a form selected from the group consisting of a nasal spray, a nasal drop, a powder, a granule, a cachet, a tablet, an aerosol, a paste, a cream, a gel, an ointment, a salve, a foam, a paste, a lotion, a cream, an oil suspension, an emulsion, a solution, a patch, and a stick. In other aspects, the prodrug of propofol is administered sublingually in a form selected from the group consisting of a tablet, a capsule, a lozenge, a sublingual spray, a mouth wash, a solution, a suspension, an emulsion, a powder, a granule, a thin film, a gel, and the like. In yet other aspects, the prodrug of propofol is administered buccally in a form selected from the group consisting of a tablet, a capsule, a lozenge, a buccal spray, a mouth wash, a solution, a suspension, an emulsion, a powder, a granule, a thin film, a gel, and the like.

In certain aspects, the subject is afflicted with a condition selected from the group consisting of a migraine, nausea, emesis, pain, analgesia, pruritis, epilepsy, headache, and anxiety. In particular aspects, the headache is a cluster headache.

In other aspects, the presently disclosed subject matter provides a pharmaceutical composition for buccally, sublingually, or intranasally administering a prodrug of propofol, or a pharmaceutically acceptable salt thereof, to a subject in need of treatment thereof in an amount sufficient to deliver a therapeutically effective amount of propofol to the subject.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

The patent or application file contains at least one drawing executed in color. Copies of this patent or patent application publication with color drawings will be provided by the Office upon request and payment of the necessary fee.

Figure 1A:
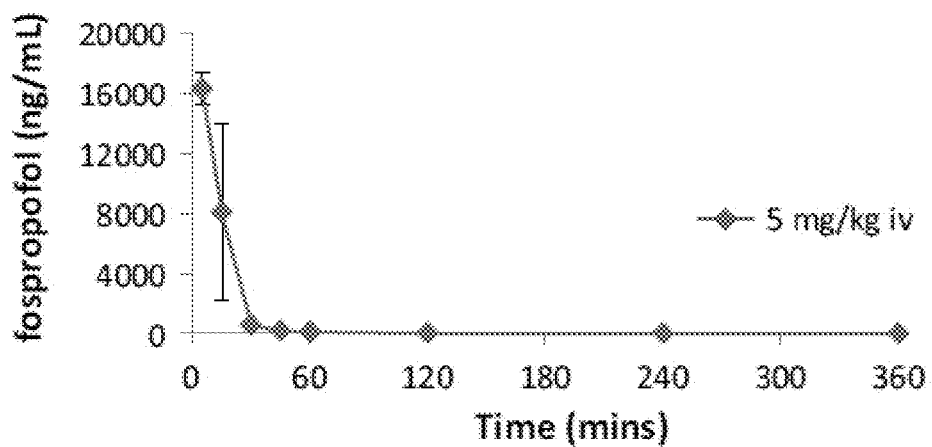
Figure 1B:
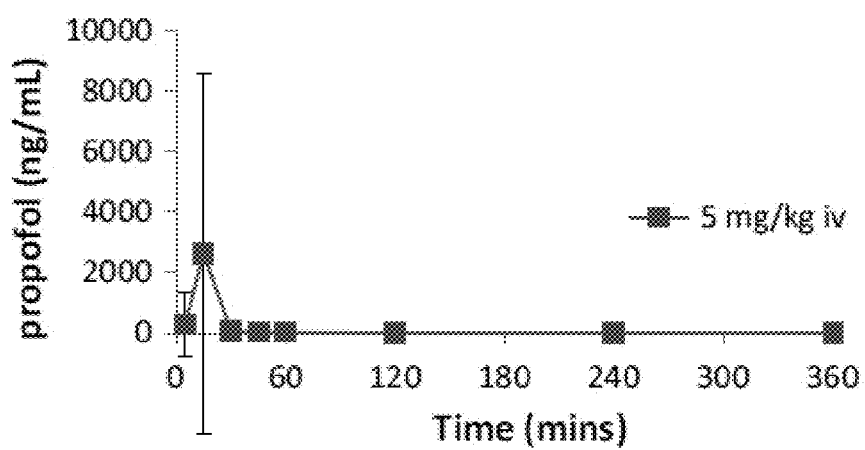
Figure 1C:
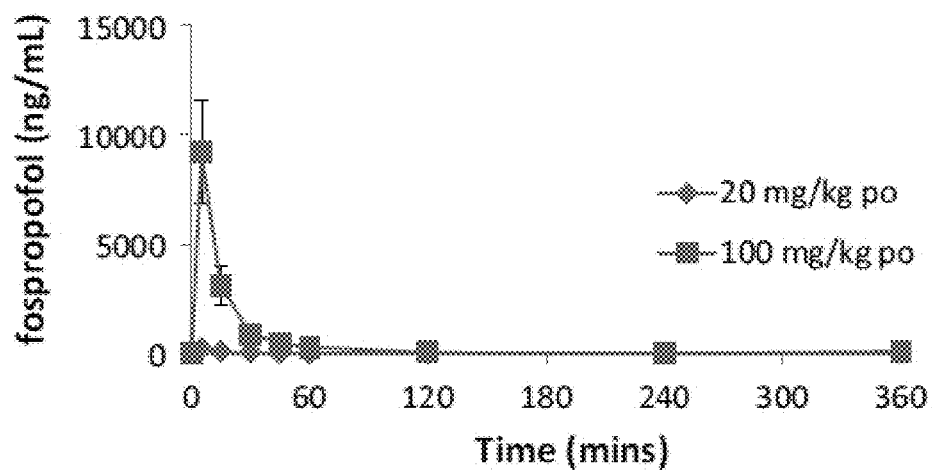
Figure 1D:
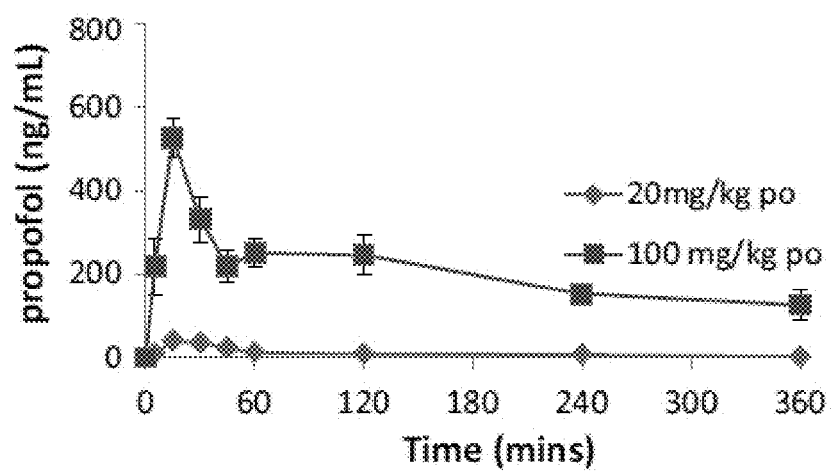
Figure 1E:
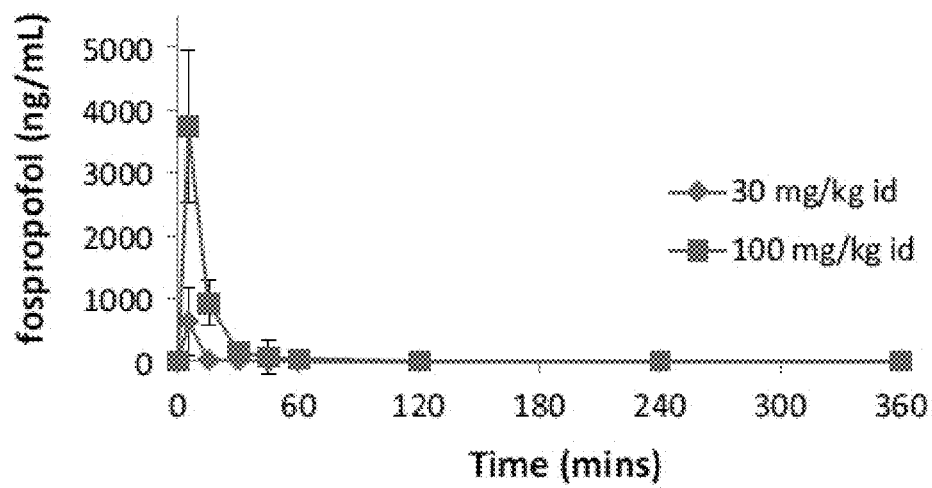
Figure 1F:
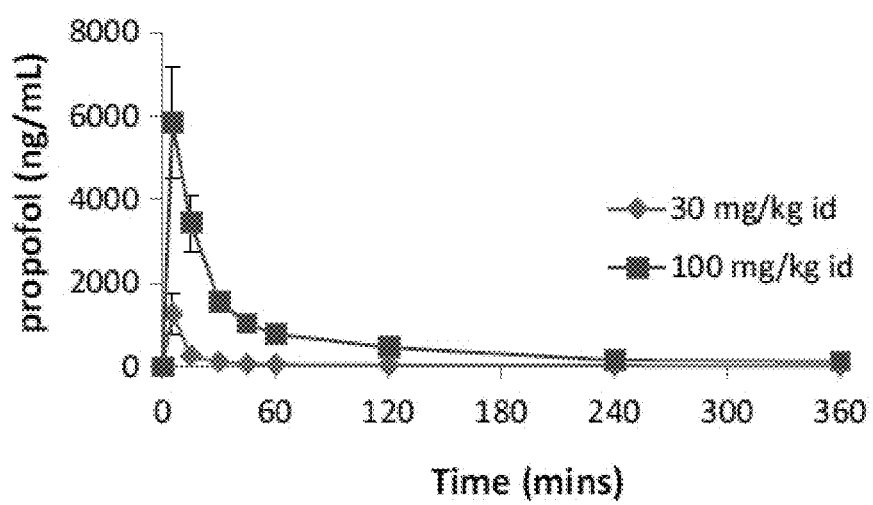
Figure 2A:
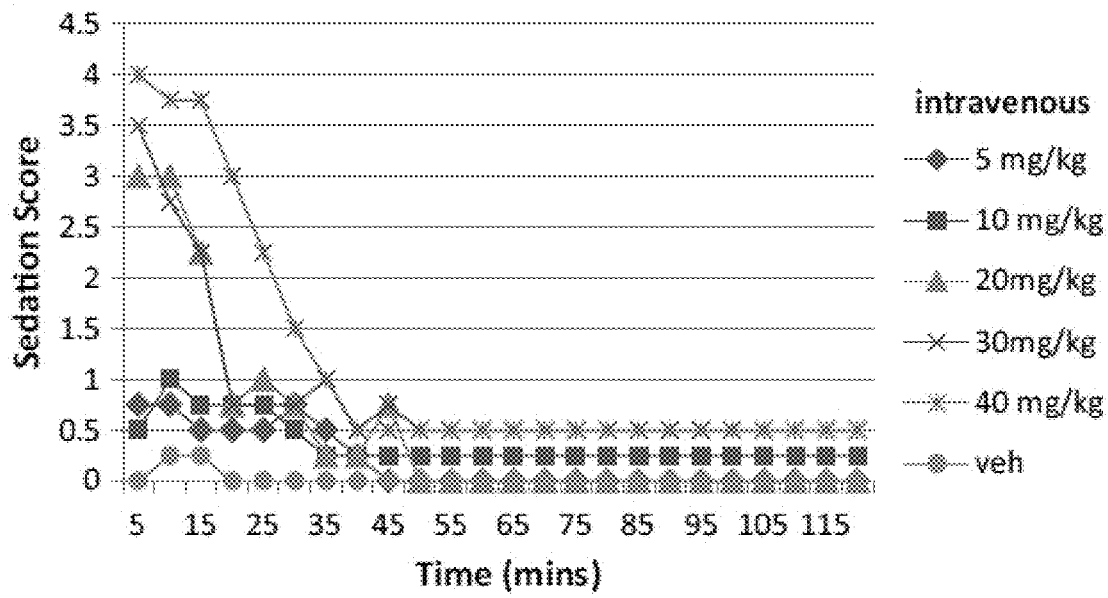
Figure 2B:
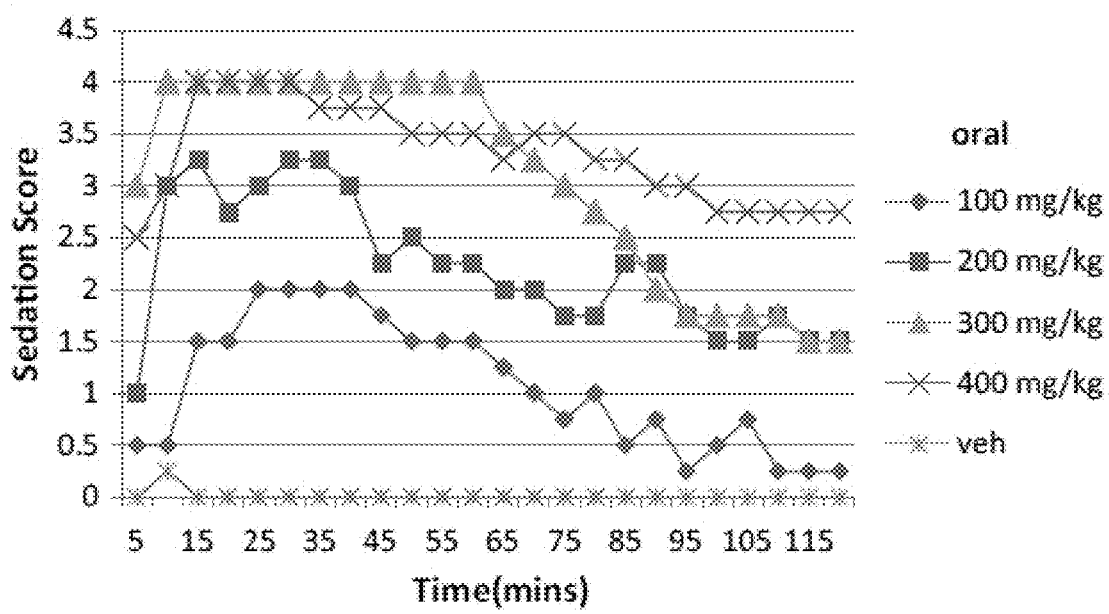
Figure 2C:
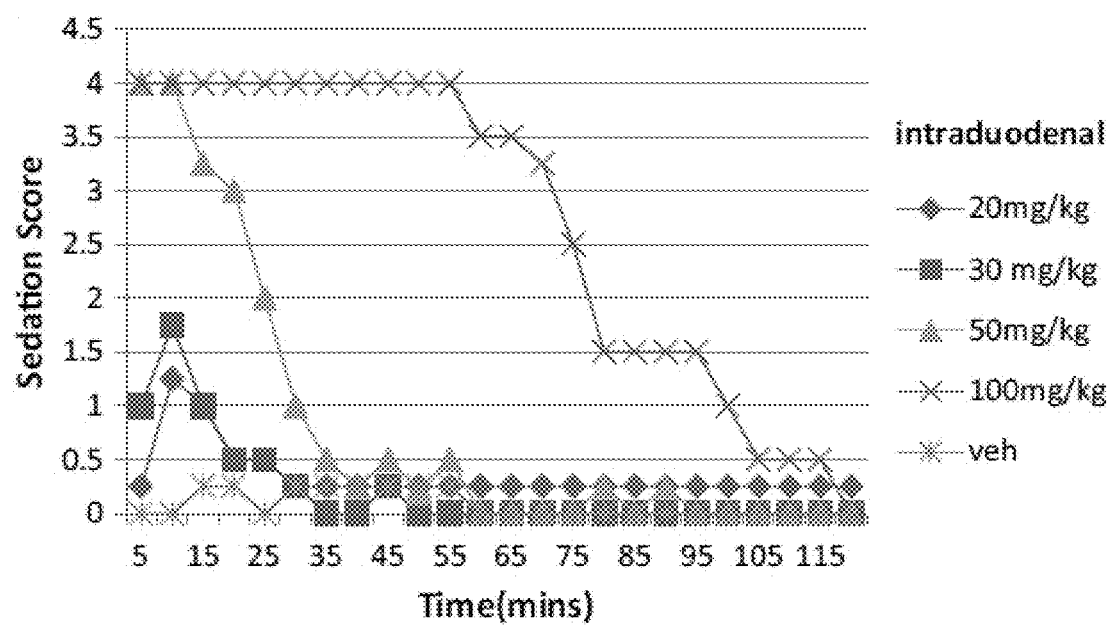
Figure 3A:
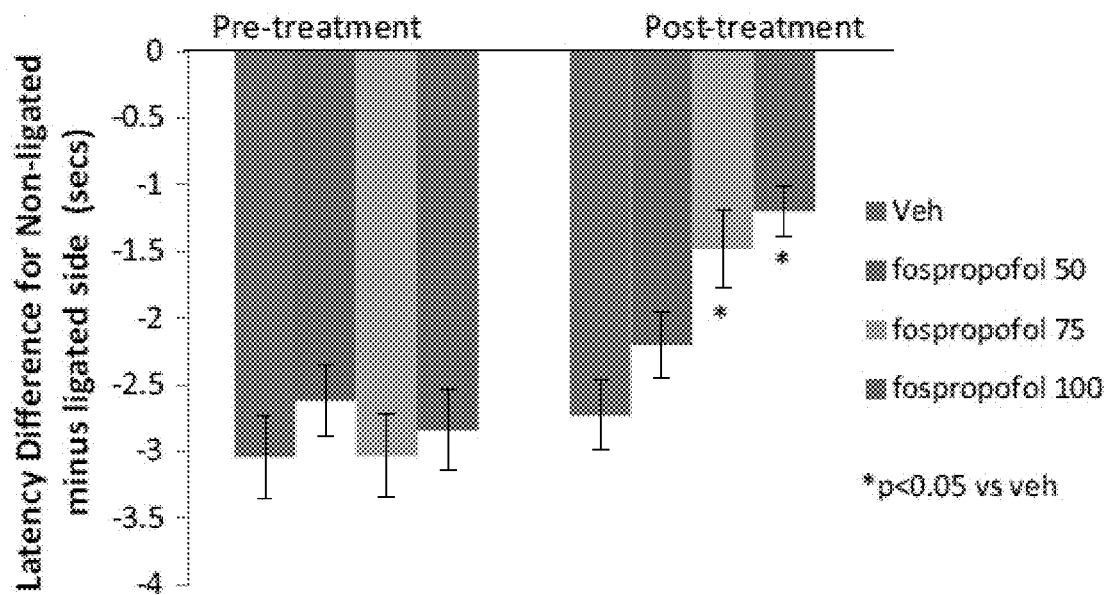
Figure 3B:
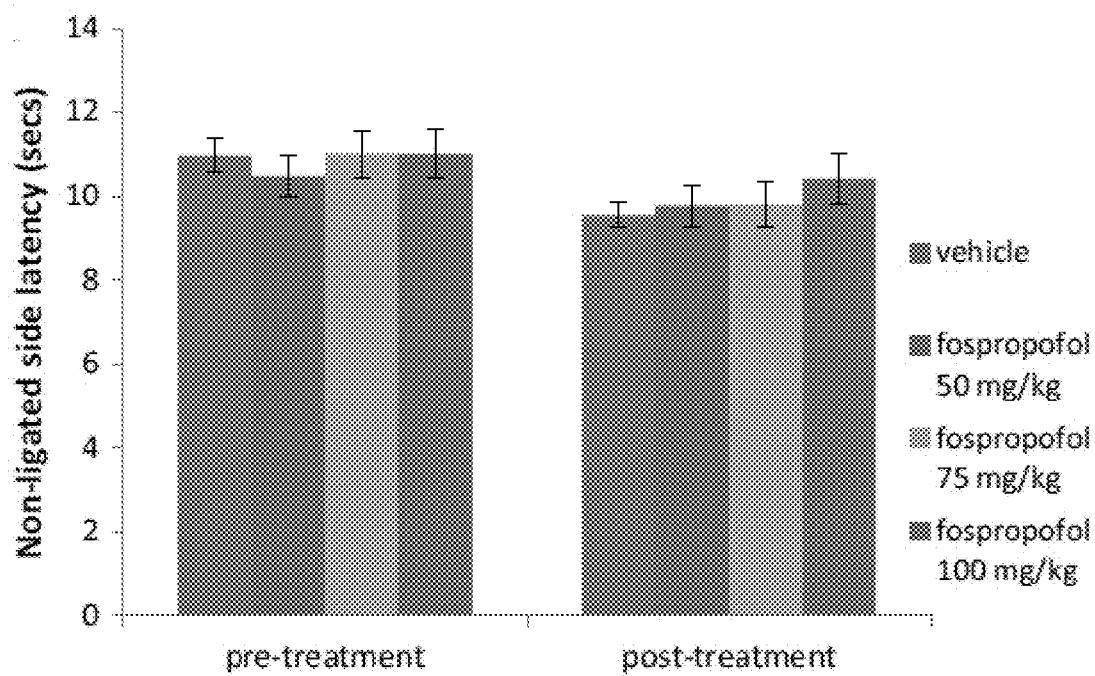
Figure 4A:
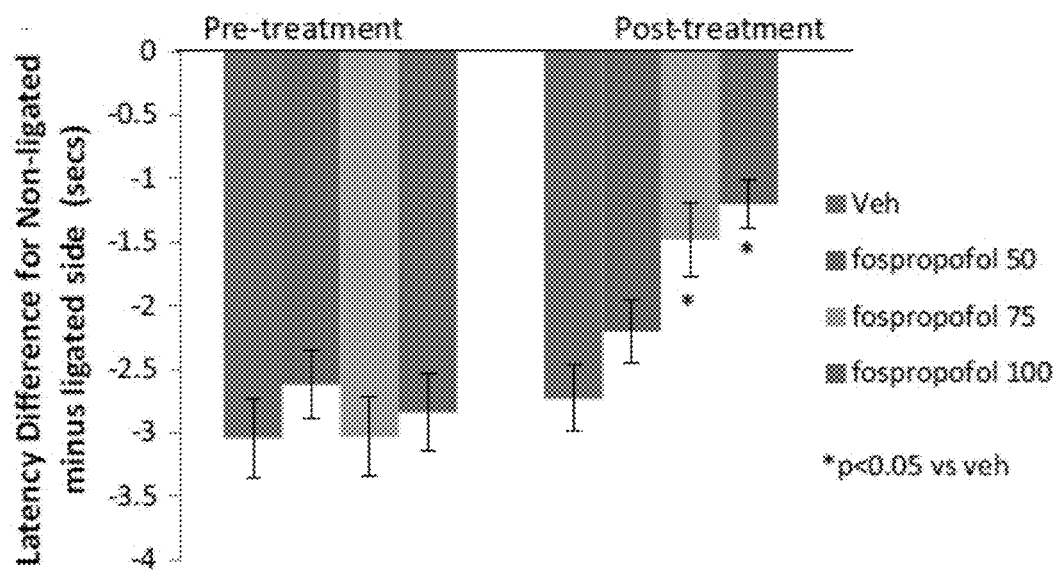
Figure 4B:
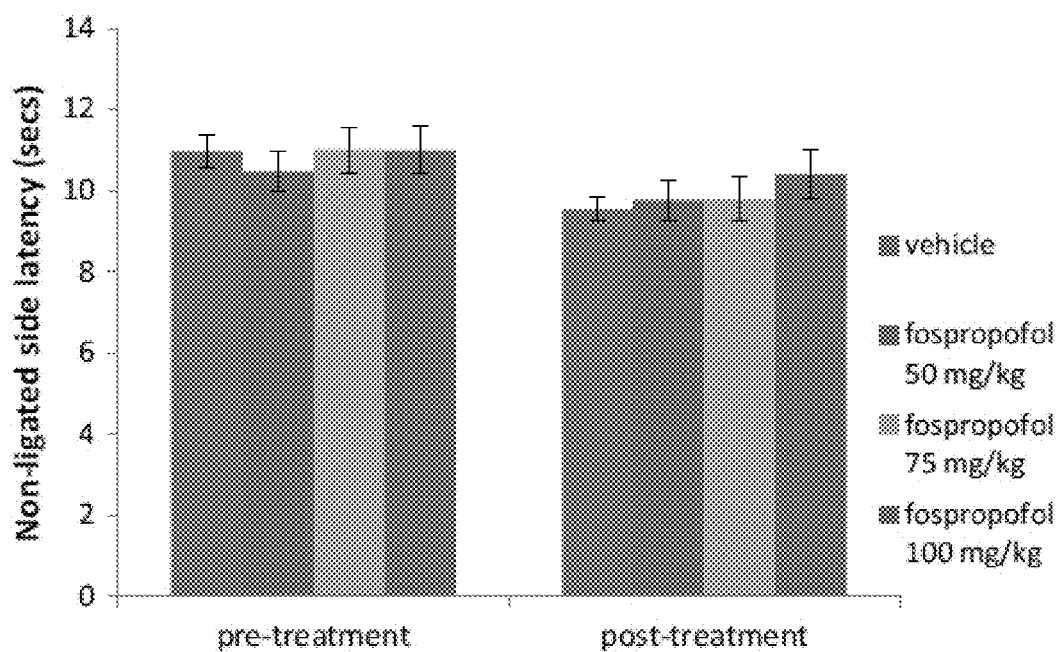
Figure 5A:
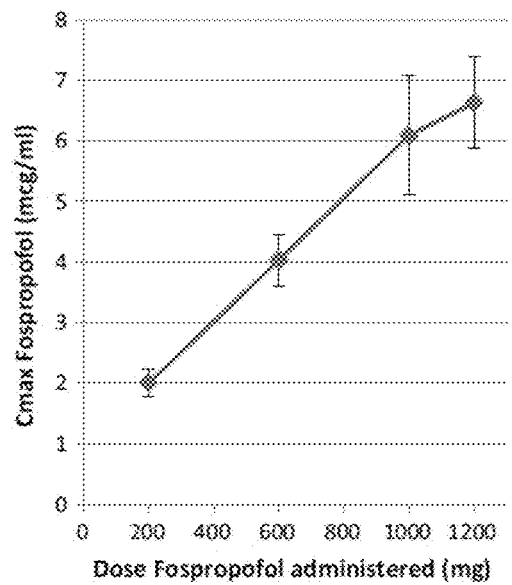
Figure 5B:
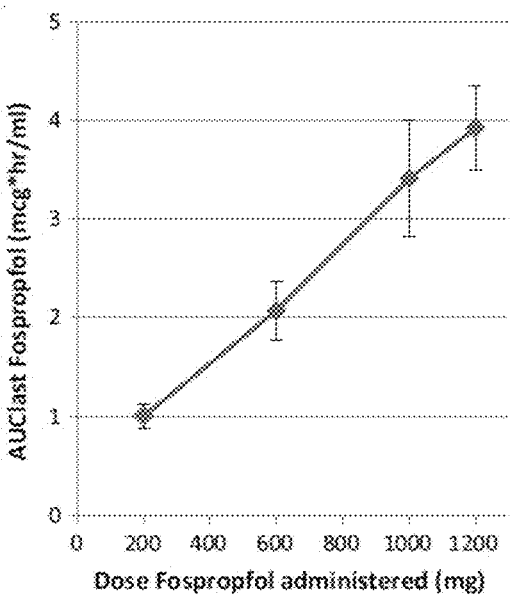
Figure 5C:
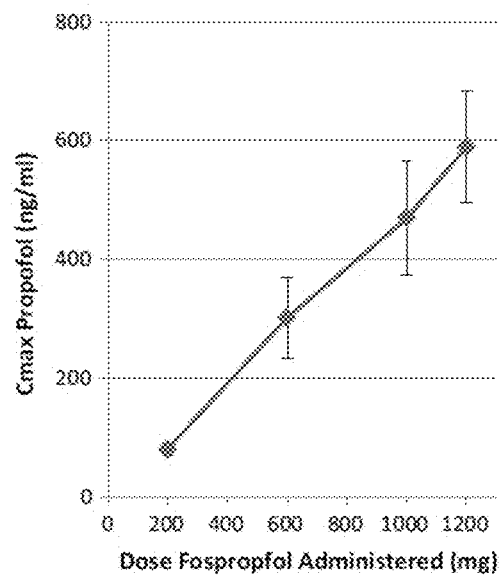
Figure 5D:
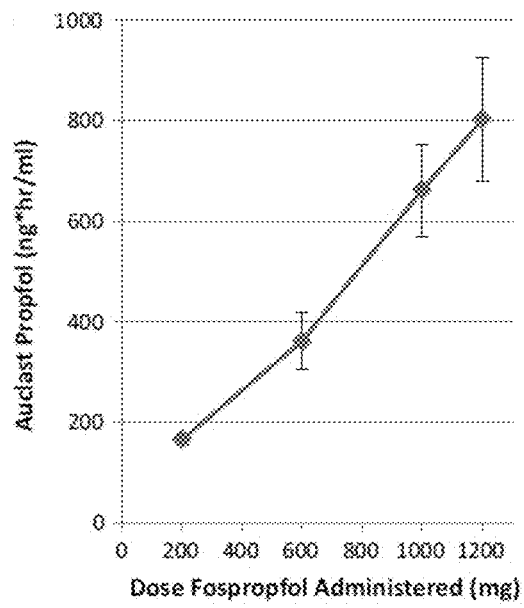
Figure 6:
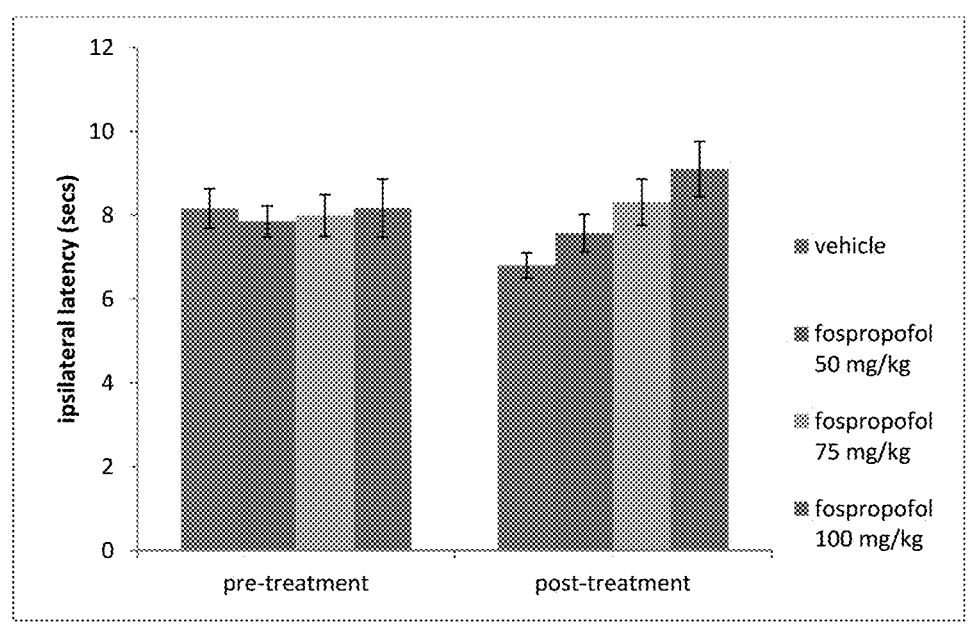
Figure 7:
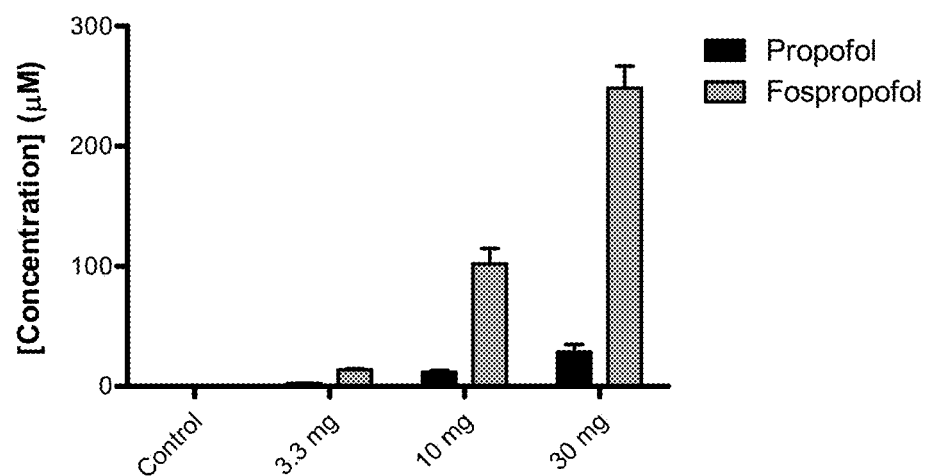
Figure 8:
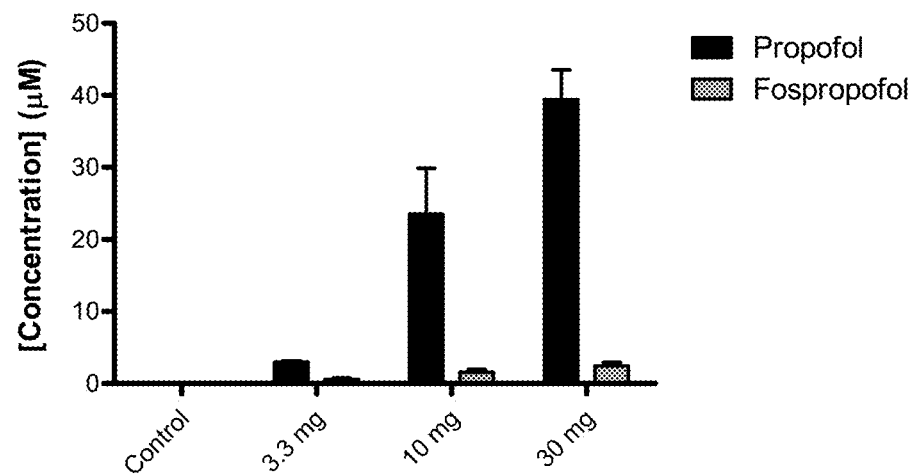
Figure 9:
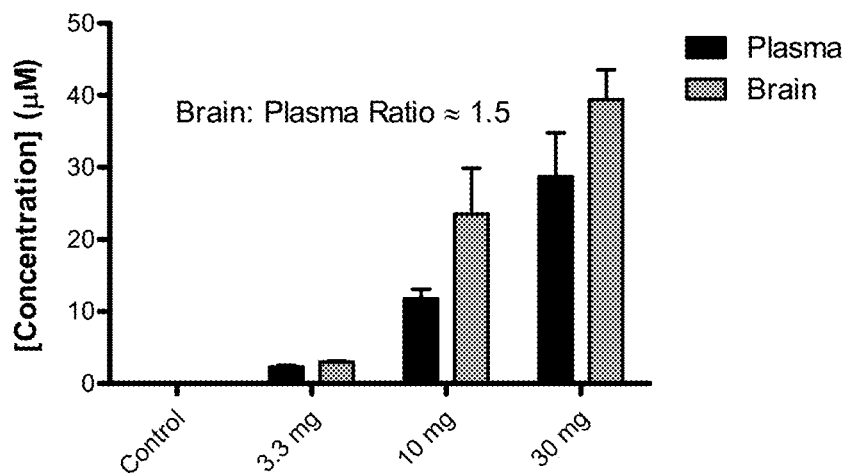
Figure 10:
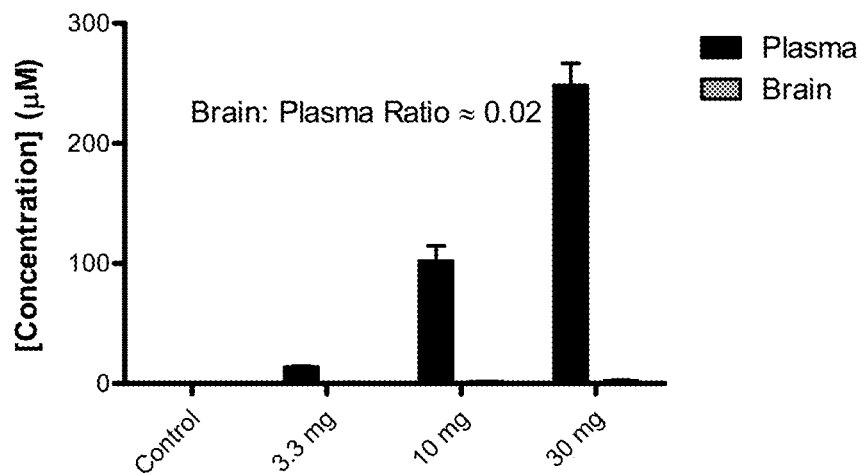
Figure 11A:
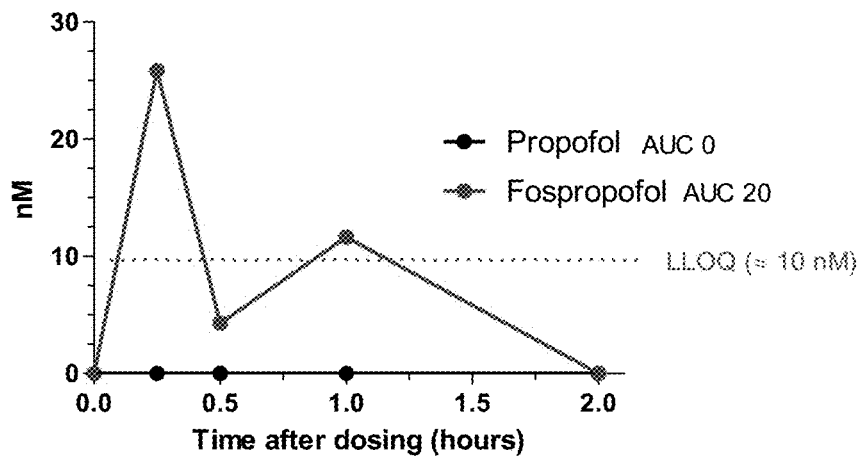
Figure 11B:
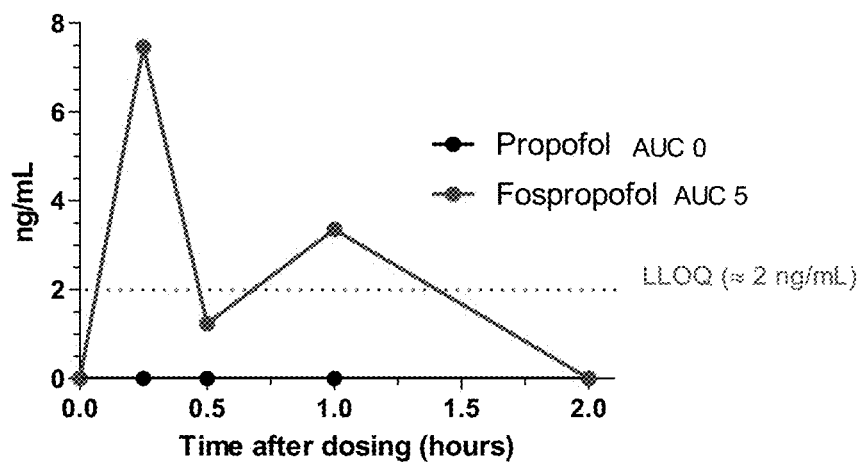
Figure 12A:
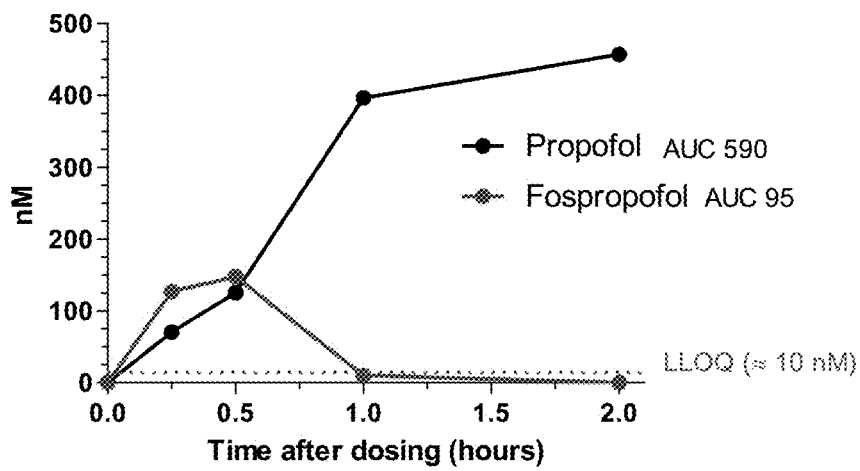
Figure 12B:
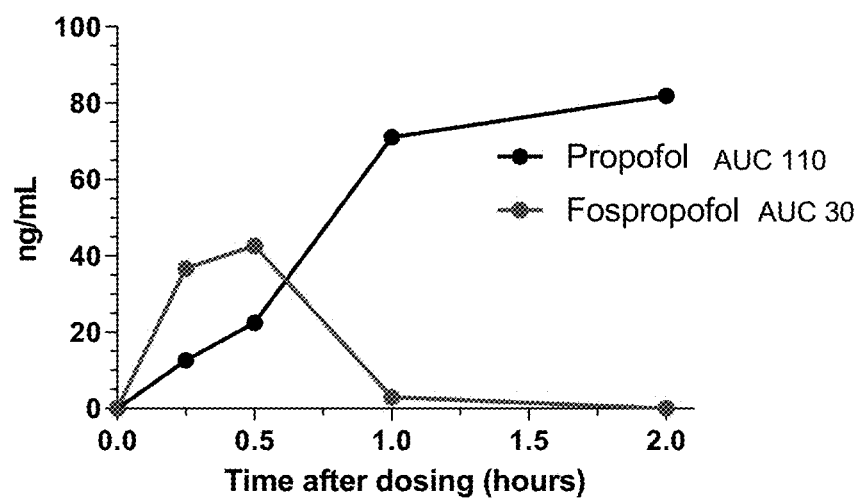
Figure 13A:
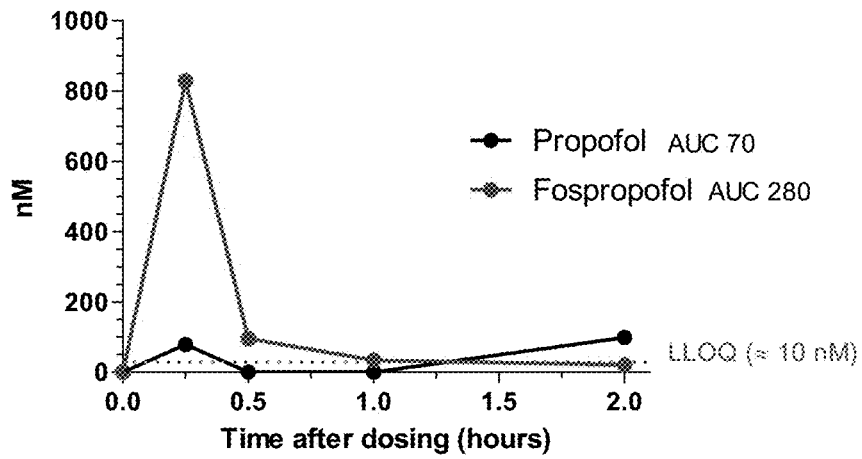
Figure 13B:
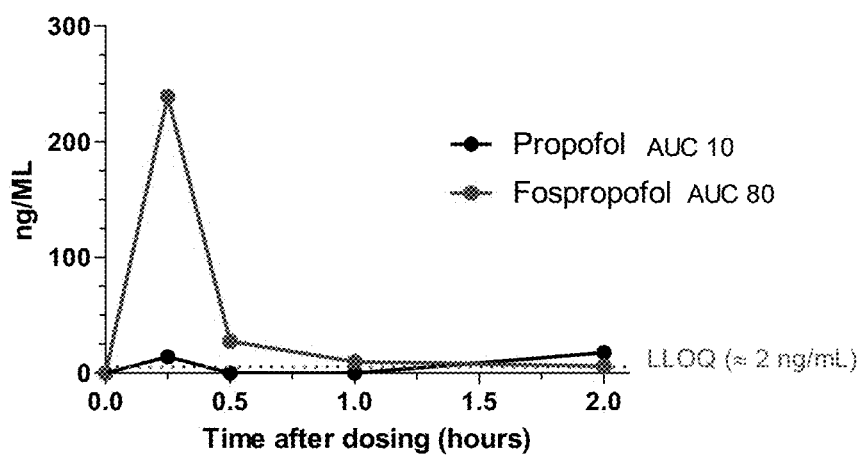

Having thus described the presently disclosed subject matter in general terms, reference will now be made to the accompanying Figures, which are not necessarily drawn to scale, and wherein:

FIG. 1A, FIG. 1B, FIG. 1C, FIG. 1D, FIG. 1E, and FIG. 1F show plasma-concentration-time curves of fospropofol and propofol after intravenous, oral and intraduodenal administration of fospropofol to rats. Intravenous administration of fospropofol (5 mg/kg) resulted in the expected immediate high concentrations of both fospropofol (FIG. 1A) and propofol (FIG. 1B). Oral administration of higher doses of fospropofol (20 or 100 mg/kg) resulted in lower peak fospropofol plasma exposure (FIG. 1C), but significant and prolonged propofol exposure (FIG. 1D). Intraduodenal administration of high doses (30 or 100 mg/kg) resulted in similar fospropofol levels in the plasma (FIG. 1E), but relatively higher peak propofol exposure (FIG. 1F). Data shown as mean±SEM;

FIG. 2A, FIG. 2B, and FIG. 2C show sedation induced by fospropofol administered via IV (FIG. 2A), PO (FIG. 2B), and ID routes (FIG. 2C). The scoring system was on a 0-4 scale, where 0=alert and completely responsive, 1=alert but less active and 'wobbly', 2=awake but drowsy with periods of inactivity, 3=generally sedated/inactive but readily arousable, and 4=unresponsive or unconscious. Sedative activity was assessed by blinded observers in 2-3 rats per treatment group;

FIG. 3A and FIG. 3B show the analgesic effect of orally administered fospropool in rat chronic constrictive injury model of neuropathic pain. Withdrawal latency measurements were taken starting 45-60 min post-dose. Fospropofol was effective in reducing hyperalgesia at doses of 75 and 100 mg/kg (FIG. 3A). This effect was not due to a non-selective sedative effect as latency on the non-ligated side did not change with fospropofol treatment (FIG. 3B). n=10 rats per group. p<0.05 vs vehicle noted as "*". Data shown as mean±SEM;

FIG. 4A and FIG. 4B show the pharmacokinetic profile of mean (±SEM) fospropofol and propofol concentrations in plasma following administration of fospropofol to human subjects by PO, IV and ID routes. A single dose of 400 mg was administered to seven volunteers in a sequential crossover design. Almost no plasma fospropofol was detected when administered by any non-intravenous route (FIG. 4A). In contrast, propofol bioavailability from fospropofol was substantial, ranging between 34 and 48% respectively by AUC (FIB. 4B). Data shown as mean±SEM;

FIG. 5A, FIG. 5B, FIG. 5C, and FIG. 5D show pharmacokinetic parameters of $AUC_{last}$ and $C_{max}$ for fospropofol (FIG. 5B and FIG. 5A) and propofol (FIG. 5D and FIG. 5C) following oral administration of placebo or fospropofol at 200, 400, 600, 1,000 and 1,200 mg in human subjects (n=10). Each subject received each of the doses. In general, dose proportional plasma concentrations of both fospropofol and propofol were observed. Data shown as mean±SEM; and FIG. 6 shows rats subjected to CCI showed similar withdrawal latency on ligated side prior to fospropofol treatment (pretreatment). Following fospropofol administration, the absolute latency of the ligated side showed a dose dependent increase compared to vehicle treatment (posttreatment). Testing was performed prior to dosing and 1 hour following oral fospropofol or vehicle treatment;

FIG. 7 shows the concentration (μM) of propofol and fospropofol in rat plasma 10 minutes after intranasal treatment with fospropofol;

FIG. 8 shows the concentration (μM) of propofol and fospropofol in rat brain 10 minutes after intranasal treatment with fospropofol;

FIG. 9 shows the fospropofol brain:plasma ratio in rat 10 minutes after intranasal treatment with fospropofol;

FIG. 10 shows the fospropofol brain:plasma ratio in rat 10 minutes after intranasal treatment with fospropofol;

FIG. 11A and FIG. 11B show the fospropofol and propofol instranasal-cerebrospinal fluid (CSF) levels in monkeys dosed with 50 mg fospropofol; and FIG. 12A and FIG. 12B show the fospropofol and propofol buccal-plasma levels in monkeys dosed with 50 mg fospropofol; and FIG. 13A and FIG. 13B show the fospropofol and propofol buccal-cerebrospinal fluid (CSF) levels in monkeys dosed with 50 mg fospropofol.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Buccal, Sublingual and Intranasal Delivery of Fospropofol

Propofol (2, 6-diisopropylphenol) is an intravenous short-acting anesthetic agent that has gained wide acceptance for inducing and maintaining anesthesia and for procedural sedation.

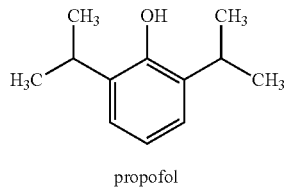

propofol

Animal and clinical data suggest that propofol has a variety of non-hypnotic effects that may have therapeutic applications at non-sedative doses (Vasileiou, et al., 2009; Borgeat, et al., 1994). Propofol also has a diverse pharmacology that might prove useful in several conditions, including prolongation of inhibitory postsynaptic currents mediated by GABA A receptors (Orser, et al., 1994), as well as enhancing GABA release via presynaptic mechanisms (Murugaiah, et al., 1998).

Potential clinical utility for propofol has been reported in various conditions including anxiety (Pain, et al., 1999; Kurt, et al., 2003), migraine (Krusz, et al., 2000; Soleimanpour, et al., 2012; Soleimanpour, et al., Int J. Emerg Med, 2012; Sheridan, et al., 2012), analgesia (Zacny, et al., 1996; Nishiyama, et al., 2004), emesis (Unlugenc, et al., 2004; DeBalli, 2003) and pruritus (Kam, et al., 1996; Borgeat, et al., 1992; Borgeat, et al., 1993), all at exposures below those causing sedation.

In spite of this potentially useful and unique pharmacology, the clinical use of propofol in other therapeutic areas has been limited by its formulation as a short-acting intravenous emulsion. Propofol's insolubility in water requires its formulation in a lipid emulsion (Mueller, et al., 2010) using complicated manufacturing processes with ensuing limited storage time because of the risk of microbial contamination (Mahajan, et al., 2012). Propofol is not orally bioavailable in animals or in humans (Glen, et al., 1985; Contreras, et al., 2011) possibly due to limited aqueous solubility and first pass metabolism by the liver. It has been reported that intravenous administration of the lipid emulsion undergoes an extraction of 80% by the liver in animals (Cozanitis, et al., 1991; Raoof, et al., 1996; Ceriana, et al., 1996) and in humans (Hiraoka, et al., 2005; Hiraoka, et al., 2004).

The development of water soluble and stable prodrugs of propofol has been described in U.S. Pat. No. 6,204,257 to Stella et al., which is incorporated herein by reference in its entirety. Such prodrugs differ from propofol in that the 1-hydroxy-group of propofol is replaced with a phosphonooxymethyl ether group and can be exemplified by compounds of Formula (I):

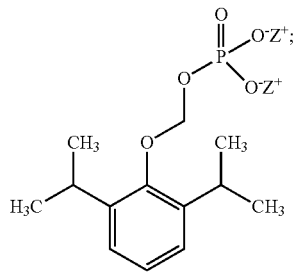

wherein each Z is independently selected from the group consisting of hydrogen, an alkali metal, and an amine. The alkali metal can be selected from the group consisting of sodium and potassium. In particular embodiments, the alkali metal is sodium.

Without wishing to be bound to any one particular theory, the prodrug is believed to undergo hydrolysis by endothelial cell surface alkaline phosphatases to release propofol. Stella reports that the prodrug has good stability at pH levels suitable for making pharmaceutical formulations and quickly breaks down in vivo under physiological conditions when administered intravenously.

More particularly, fospropofol (Lusedra®, Eisai, Inc., Woodcliff Lake, N.J., USA) is a water-soluble, phosphono-O-methyl prodrug of propofol that was approved as an alternative to propofol for monitored anesthesia care during procedures in the United States (Mahajan, et al., 2012; Mahajan, et al., J Anaesthesiol Clin Pharmacol, 2012). The aqueous solubility of fospropofol allows it to be formulated for intravenous use without the oil-in-water emulsion formulation required for propofol. Fospropofol is rapidly metabolized by endothelial alkaline phosphatases to release propofol, phosphate and formaldehyde. Formaldehyde is rapidly converted to formate and safely eliminated, similar to the other available phosphate methyl prodrugs, such as fosphenytoin. Sedative effects appear to be due entirely to the propofol liberated from the prodrug. Prodrug metabolism, however, leads to differences from propofol in its onset, peak effects and duration of action (Mahajan, et al., 2012; Fechner, et al., 2003; Welliver, et al., 2009). Fospropofol was generally well tolerated in clinical trials with only mild to moderate adverse events reports, mostly transient in nature (Garnock-Jones, et al., 2010). Thus, as an intravenous sedative, fospropofol has several advantages over propofol, including less pain at site of injection, less potential for hyperlipidemia with long-term use and less chance of bacteremia in patients.

The presently disclosed subject matter, in part, demonstrates, whether a compound of Formula (I), which in some embodiments comprises fospropofol (a water soluble phosphate ester prodrug of propofol), provides higher propofol bioavailability through non-intravenous routes, including buccal, sublingual and intranasal delivery.

As used herein, the term "prodrug" refers to a compound that readily undergoes chemical changes under physiological conditions to provide the active agent in vivo. In particular embodiments, the prodrug is fospropofol disodium. Generally, certain biologically active compounds are better absorbed through the mucosa than through other routes of administration, such as through the stomach or intestine. Transmucosal absorption allows permeation of drugs directly into the bloodstream and then into the cells within a matter of minutes. Within the oral cavity cavity, for example, a number of mucosal surfaces may be used to deliver pharmaceuticals, including but not limited to: (i) sublingual surfaces, i.e., the mucosal membranes lining the floor of the mouth, (ii) buccal surfaces, i.e., the mucosal membranes lining the cheeks, (iii) lingual surfaces, i.e., the surface membranes of the tongue, (iv) palatal surfaces, i.e., the membranes lining the roof of the mouth, (v) pharyngeal surfaces, i.e., the membranes of the pharynx, (vi) gingival mucosa, i.e., the gums, and (vii) gingival sulcus, i.e., the cavity formed between the teeth and gums.

More particularly, buccal, sublingual, or intranasal administration generally allows the active agent to bypass first pass metabolism, thereby enhancing the bioavailability of the active agent. Such delivery can offer several advantages over other modes of drug delivery, including, but not limited to, increasing the onset of action, lowering the required dosage, enhancing the efficacy, and improving the safety profile of the active agent. For example, tablet dosage forms enter the bloodstream through the gastrointestinal tract, which subjects the drug to degradation from stomach acid, bile, digestive enzymes, and other first pass metabolism effects. As a result, tablet formulations often require higher doses and generally have a delayed onset of action. Buccal, sublingual or nasal administration of a drug also can facilitate compliance, especially for pediatric patients, geriatric patients, patients suffering from a neurodegenerative disease, or other patients for which swallowing is difficult, e.g., patients suffering from nausea, such as patients undergoing chemotherapy, or patients with a swallowing disorder.

As used herein and unless otherwise indicated, the term "buccal mucosa" refers to oral mucosal membranes lining the cheeks. Likewise, the term "nasal mucosa" refers to mucosal membranes lining the nasal cavity.

As used herein and unless otherwise indicated, the term "sublingual" means relating to the area of the oral cavity below the tongue.

As used herein and unless otherwise indicated, the terms "transmucosal oral administration" and "transmucosal oral administration" include any method of administering an active agent to the oral cavity or nasal cavity of a subject in which a substantial portion of the active agent enters the blood stream of the subject by diffusion or movement through any of the mucus membranes of the oral cavity or nasal cavity, respectively.

Accordingly, in some embodiments, the presently disclosed subject matter provides a method for buccally, sublingually or intranasally administering a prodrug of propofol, or a pharmaceutically acceptable salt thereof, to a subject in need of treatment thereof in an amount sufficient to deliver a therapeutically effective amount of propofol to the subject.

In other embodiments, the prodrug of propofol is a compound of Formula (I).

In particular embodiments, the transmucosal administration of fospropofol comprises administering the fospropofol buccally, sublingually, or intranasally.

In yet more particular embodiments, the prodrug of propofol, or pharmaceutical composition thereof, is administered intranasally in a form selected from the group consisting of a nasal spray, a nasal drop, a powder, a granule, a cachet, a tablet, an aerosol, a paste, a cream, a gel, an ointment, a salve, a foam, a paste, a lotion, a cream, an oil suspension, an emulsion, a solution, a patch, a stick, and the like.

Formulations for nasal administration may be solutions in evaporating solvents, including, but not limited to, hydrofluorocarbons, and may contain excipients for stabilization, for example, saccharides, surfactants, submicron anhydrous α-lactose or dextran, or may be aqueous or oily solutions for use in the form of nasal drops or metered spray, e.g., via a metered-dose inhaler.

In certain embodiments, the method comprises administering the prodrug of propofol via a buccal, sublingual, or nasal spray composition. In some embodiments, the buccal, sublingual, or nasal spray composition comprises a propellant. In particular embodiments, the propellant is selected from the group consisting of a hydrofluorocarbon, a linear or branched $C_3$ to $C_8$ hydrocarbon, and combinations thereof. In yet more particular embodiments, the linear or branched $C_3$ to $C_8$ hydrocarbon is elected from the group consisting of propane, n-butane, iso-butane, n-pentane, iso-pentane, neopentane, and combinations thereof.

In some embodiments, the buccal, sublingual or nasal spray composition comprises a polar solvent. In particular embodiments, the polar solvent is selected from the group consisting of water, linear or branched $C_2$ to $C_{18}$ alcohols, $C_2$ to $C_8$ polyalcohols, polyethyleneglycols, and combinations thereof.

In other embodiments, the buccal, sublingual, or nasal spray composition comprises an absorption or permeability enhancing agent. In particular embodiments, the absorption or permeability enhancing agent is selected from the group consisting of oleic acid, 23-lauryl ether, aprotinin, azone, benzalkonium chloride, cetylpyridinium chloride, cetyltrimethylammonium bromide, cyclodextrin, dextran sulfate, lauric acid, lauric acid/propylene glycol, lysophosphatidylcholine, menthol, methoxysalicylate, methyloleate, phosphatidylcholine, polyoxyethylene, polysorbate 80, sodium EDTA (ethylenediamine tetraacetic acid), sodium glycocholate, sodium glycodeoxycholate, sodium lauryl sulfate, sodium salicylate, sodium taurocholate, sodium taurodeoxycholate, sulfoxides, an alkyl glycoside, and combinations thereof.

In yet other embodiments, the buccal, sublingual, or nasal spray composition further comprises an antioxidant. In particular embodiments, the antioxidant is selected from the group consisting of ascorbyl palmitate, alpha tocopherol, butylated hydroxyanisole, fumaric acid, and combinations thereof.

In some embodiments, the buccal, sublingual or nasal spray composition further comprises a flavoring agent. In particular embodiments, the flavoring agent is selected from the group consisting of synthetic or natural oil of peppermint, one or more citrus oils, one of more fruit flavors, one or more sweeteners, and combinations thereof.

In other embodiments, the prodrug of propofol, or pharmaceutical composition thereof, is administered buccally or sublingually in a form selected from the group consisting of a tablet, a capsule, a lozenge, a buccal spray, a mouth wash, a solution, a suspension, an emulsion, a powder, a granule, a thin film, a gel, and the like.

For buccal or sublingual administration, typical excipients include sugars, calcium stearate, magnesium stearate, pregelatinated starch, and the like. Such compositions also can include sweetening agents, saliva stimulating agents, flavoring agents, coloring agents, stabilizing and thickening agents, permeability enhancing agents, and the like.

Further, for nasal, sublingual, or buccal administration, transmucosal penetrants can be used in the formulation. Such penetrants are generally known in the art and can include nanoparticle formulations, see e.g., U.S. Pat. No. 9,327,037 for "Mucus Penetrating Gene Carriers" to Suk and Hanes, issued May 3, 2016.

In certain embodiments, the subject is afflicted with a condition selected from the group consisting of a migraine, nausea, emesis, pain, analgesia, pruritis, epilepsy, headache and anxiety. In particular embodiments, the headache is a cluster headache.

The prodrug of propofol, or a pharmaceutically acceptable salt thereof, may be administered by itself or it may be co-administered together with one or more additional active agents. Non-limiting examples of additional active agents include, without limitation, hypnotic, analgesic, anti-inflammatory, amnesic, muscle relaxant, and sedative agents. Such additional active agents may be incorporated into a single pharmaceutical composition containing the prodrug of propofol for buccal, sublingual or intranasal administration or may be administered in a separate pharmaceutical formulation by any suitable route.

In some embodiments, a conscious sedated state in a subject can be induced or maintained over an extended period of time by buccal, sublingual or intranasal administration of a therapeutically effective amount of a prodrug of propofol, or a pharmaceutically acceptable salt thereof.

In other embodiments, a somnolent state is induced or maintained in a subject over an extended period of time by buccal, sublingual or intranasal administration of a therapeutically effective amount of a prodrug of propofol, or a pharmaceutically acceptable salt thereof.

Appropriate exemplary dose levels for inducing or maintaining a somnolent state in a subject by single or repeated buccal, sublingual or intranasal administration of a prodrug of propofol, or a pharmaceutically acceptable salt thereof, range, in some embodiments, from about 10 mg/kg to about 400 mg/kg, in other embodiments, from about 20 mg/kg to about 300 mg/kg, and in yet other embodiments, from about 25 mg/kg to about 250 mg/kg. Dose levels sufficient to induce a conscious sedated state overlap with doses sufficient to induce a somnolent state, and range, in some embodiments, from about 15 mg/kg to about 500 mg/kg, in other embodiments, from about 20 mg/kg to about 500 mg/kg, and in yet other embodiments, from about 30 mg/kg to about 400 mg/kg.

The induction or maintenance of a somnolent state, experienced as, e.g., a relaxed and mildly drowsy inclination to sleep, are desirable, for example, in individuals suffering from insomnia or another condition characterized by increased and inappropriate wakefulness relative to the demands of society, such as, circadian rhythm sleep disorders (e.g., delayed sleep phase disorder, "jet lag", or "shift work" type sleep disorder). Optionally, buccal, sublingual or intranasal doses of the prodrug of propofol can be adjusted to treat specific aspects of the sleep disorder, such as sleep latency, depth of sleep, or duration of sleep. For therapeutic use, the prodrug of propofol can be administered singly, or in combination with other agents useful in the therapy of sleep disorders, combined in a single formulation or separately.

Dose levels sufficient to induce a conscious sedated state or a somnolent state are further useful in the treatment of anxiety in subjects in need of such treatment, as will be appreciated by those skilled in the art. Thus, anxiolytically effective doses of the prodrug of propofol will be coextensive with doses which themselves cause conscious sedation or mild to moderate sleepiness, and can be administered buccally or intranasally to a subject in need of anxiolytic therapy.

Those skilled in the art will appreciate that prodrugs of propofol, while being useful in the induction and maintenance of anesthesia, sedation, sleep, and anxiolysis as described hereinabove, also are useful in treating other medical conditions known to be amenable to treatment with propofol. Accordingly, in some embodiments, the presently disclosed subject matter provides a method for suppressing nausea or vomiting in a subject, wherein the prodrug of propofol, or a pharmaceutically acceptable salt thereof, is buccally or intranasally administered to a subject in an amount sufficient to suppress nausea or vomiting. While the presently disclosed method is useful in suppressing nausea and vomiting in a variety of situations, such as, for example where the subject suffers from motion sickness, it also has applications in settings where the subject suffers from, or is at risk of, nausea or vomiting related to cancer chemotherapy or radiation therapy, or where the subject suffers from postoperative nausea and vomiting. In such embodiments, the the prodrugs of propofol are preferably administered at subhypnotic doses, i.e., the dose of the prodrug of propofol, whether administered buccally or intranasally, does not cause loss of consciousness, and, if the subject also is not in need of sedation; preferably does not cause a sedated state. For example, appropriate doses for suppressing or alleviating nausea and vomiting in a subject by single or repeated buccal, sublingual or intranasal administration of a prodrug of propofol range, in some embodiments, from about 0.5 mg/kg to about 450 mg/kg, in other embodiments, from about 1 mg/kg to about 400 mg/kg, and, in yet other embodiments, from about 5 mg/kg to about 350 mg/kg.

In another embodiment, the presently disclosed subject matter provides a method for treating itching associated with a pruritic condition in a subject, wherein a prodrug of propofol, or a pharmaceutically acceptable salt thereof, is buccally, sublingually or intranasally administered to a subject in an amount sufficient to prevent, alleviate, or suppress localized or general itching. In such embodiments, prodrugs of propofol are preferably administered at subhypnotic doses, i.e., the administered amount of the prodrug of propofol does not cause loss of consciousness, and, if the subject also is not in need of sedation, preferably does not cause a sedated state. For example, appropriate doses for suppressing or alleviating local or generalized itching in a subject by single or repeated buccal, sublingual or intranasal administration of a prodrug of propofol range, in some embodiments, from about 0.5 mg/kg to about 450 mg/kg, in other embodiments from about 1 mg/kg to about 400 mg/kg, and, in yet other embodiments, from about 5 mg/kg to about 350 mg/kg.

In yet another embodiment, the prodrug of propofol, or a pharmaceutically acceptable salt thereof, may be administered for treating subjects suffering from an epileptic condition. A subject in need of such treatment is buccally or intranasally administered a dose of a prodrug of propofol, or a pharmaceutically acceptable salt thereof, in an amount sufficient to prevent, suppress, or alleviate the epileptic condition. Suitable exemplary dosages, for treating subjects suffering from an epileptic condition range from subhypnotic doses, such as the antiemetic or antipruritic doses, as defined hereinabove, to higher, hypnotic doses, as required by the individual subject's needs. Individual suitable doses can be determined by those skilled in the art, especially in light of the guidance provided herein. A suitable dose for an unconscious subject presenting with status epilepticus, for example, may be determined and adjusted as needed by monitoring brain seizure activity on an electroencephalogram, and a suitable formulation comprising a prodrug of propofol may be administered buccally, sublingually, or intranasally.

If an epileptic condition is to be treated by single or repeated buccal, sublingual or intranasal administrations of a prodrug of propofol for example, appropriate doses typically, in some embodiments, range from about 0.5 mg/kg to 1000 mg/kg, in other embodiments, from about 2 mg/kg to about 500 mg/kg, and, in yet other embodiments, from about 5 mg/kg to about 400 mg/kg body weight.

In other embodiments, the presently disclosed subject matter provides a method for treating migraine pain, cluster headaches, and other acute headaches. Subjects in need of such treatment can be buccally or intranasally administered an effective amount of a prodrug of propofol, or a pharmaceutically acceptable salt thereof, singly, or in repeated doses until pain relief is accomplished. Exemplary suitable doses range, in some embodiments, from about 5 mg/kg to about 500 mg/kg, in other embodiments, from about 10 mg/kg to about 500 mg/kg, and, in yet other embodiments, from about 20 mg/kg to about 400 mg/kg. Since such doses overlap with the antiemetic doses provided hereinabove, they also are expected to be effective in treating nausea frequently associated with migraine pain.

As will be appreciated by those skilled in the art, pain syndromes other than acute headaches also will be treatable by buccal, sublingual or intranasal administration of the prodrugs of propofol at the dose levels provided herein, and the treatment of such other pain syndromes is intended to be within the scope of the presently disclosed subject matter. Non-limiting examples of such other pain syndromes are: trigeminal facial or dental pain; neuropathic pain associated with neuropathies caused by disease (e.g., diabetes, or viral infections, such as herpes or HIV) or drugs (e.g., taxol, cisplatin, and other anticancer agents); phantom limb pain suffered by amputees; persistent and largely intractable postoperative pain; and arthritic pain.

In yet other embodiments, the presently disclosed subject matter also provides a method for the treatment of a pathologic condition having an inflammatory component in a subject, wherein a pharmacologically effective amount of a prodrug of propofol is buccally, sublingually, or intranasally administered to the subject. This embodiment finds particular application in the treatment of a pathologic condition of the nervous system having an inflammatory component.

In another embodiment, the presently disclosed subject matter provides a method for the treatment of a pathologic respiratory condition in a subject, wherein a pharmacologically effective amount of a prodrug of propofol is buccally or intranasally administered to the subject. This embodiment finds particular application in pathologic respiratory conditions associated with oxidative tissue damage.

In another embodiment, the presently disclosed subject matter provides a method of treatment wherein a prodrug of propofol is buccally, sublingually, or intranasally administered to a subject in conjunction with a cytostatic chemotherapeutic agent, and wherein the subject suffers from cancer.

In another embodiment, the presently disclosed subject matter provides a method for treating spasticity, hyperekplexia, or of providing muscle relaxation in a subject in need thereof, which comprises buccally or intranasally administering to the subject a therapeutically effective amount of a prodrug of propofol.

In yet another embodiment, there is provided a method for preventing neurodegeneration in the central nervous system of a subject, which comprises buccally or intranasally administering to a subject suffering from, or being at risk for, neurodegeneration caused by traumatic or vascular injury, toxicity, or disease, a therapeutically effective amount of a prodrug of propofol. In some embodiments, the subject suffers from, or is at risk of, ischemic injury to the brain, for example as a result of having suffered a stroke.

The subject treated by the presently disclosed methods in their many embodiments is desirably a human subject, such as a postnatal human subject, although it is to be understood that the methods described herein are effective with respect to all vertebrate species, which are intended to be included in the term "subject." Accordingly, a "subject" can include a human subject for medical purposes, such as for the treatment of an existing disease, disorder, condition or the prophylactic treatment for preventing the onset of a disease, disorder, or condition or an animal subject for medical, veterinary purposes, or developmental purposes. Suitable animal subjects include mammals including, but not limited to, primates, e.g., humans, monkeys, apes, gibbons, chimpanzees, orangutans, macaques and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, guinea pigs, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a disease, disorder, or condition. Thus, the terms "subject" and "patient" are used interchangeably herein. Subjects also include animal disease models (e.g., rats or mice used in experiments).

As used herein, the terms "treat," treating," "treatment," and the like, are meant to decrease, suppress, attenuate, diminish, arrest, the underlying cause of a disease, disorder, or condition, or to stabilize the development or progression of a disease, disorder, condition, and/or symptoms associated therewith. The terms "treat," "treating," "treatment," and the like, as used herein can refer to curative therapy, prophylactic therapy, and preventative therapy. The treatment, administration, or therapy can be consecutive or intermittent. Consecutive treatment, administration, or therapy refers to treatment on at least a daily basis without interruption in treatment by one or more days. Intermittent treatment or administration, or treatment or administration in an intermittent fashion, refers to treatment that is not consecutive, but rather cyclic in nature. Treatment according to the presently disclosed methods can result in complete relief or cure from a disease, disorder, or condition, or partial amelioration of one or more symptoms of the disease, disease, or condition, and can be temporary or permanent. The term "treatment" also is intended to encompass prophylaxis, therapy and cure.

As used herein, the terms "prevent," "preventing," "prevention," "prophylactic treatment" and the like refer to reducing the probability of developing a disease, disorder, or condition in a subject, who does not have, but is at risk of or susceptible to developing a disease, disorder, or condition. Thus, in some embodiments, an agent can be administered prophylactically to prevent the onset of a disease, disorder, or condition, or to prevent the recurrence of a disease, disorder, or condition.

The term "effective amount," as in "a therapeutically effective amount," of a therapeutic agent refers to the amount of the agent necessary to elicit the desired biological response. As will be appreciated by those of ordinary skill in this art, the effective amount of an agent may vary depending on such factors as the desired biological endpoint, the agent to be delivered, the composition of the pharmaceutical composition, the target tissue or cell, and the like. More particularly, the term "effective amount" refers to an amount sufficient to produce the desired effect, e.g., to reduce or ameliorate the severity, duration, progression, or onset of a disease, disorder, or condition, or one or more symptoms thereof; prevent the advancement of a disease, disorder, or condition, cause the regression of a disease, disorder, or condition; prevent the recurrence, development, onset or progression of a symptom associated with a disease, disorder, or condition, or enhance or improve the prophylactic or therapeutic effect(s) of another therapy.

As skilled persons will appreciate, the prodrugs of propofol can be formulated for buccal, sublingual or intranasal administration according to methods which are well-established in the art. The skilled person is directed to widely available reference works, such as Gennaro's treatise "Remington: The Science and Practice of Pharmacy" (Lippincott, Williams and Wilkins (Pub.), 2003), or Ansel, Allen, and Popovich's treatise "Pharmaceutical Dosage Forms and Drug Delivery Systems" (Lippincott, Williams and Wilkins (Pub.), 2004), the teachings of which are herein incorporated by reference.

As will be appreciated by one of ordinary skill in the art, many factors influence the choice of appropriate dosage and schedule of administration. For example, the appropriate dosage for achieving a desired therapeutic effect in a subject may depend on whether the subject is a human, or another mammal, or is a non-mammalian subject; it may depend on the subject's age, weight, sex, diet, health, underlying medical condition, and the like. Therefore, a physician, veterinarian, or other medical, science, or health practitioner skilled in the art will be able to devise, in light of the guidance provided herein, and without undue experimentation, an appropriate treatment protocol for practicing the presently disclosed methods.

Actual dosage levels of the active ingredients in the presently disclosed pharmaceutical compositions can be varied so as to obtain an amount of the active ingredient that is effective to achieve the desired therapeutic response for a particular subject, composition, route of administration, and disease, disorder, or condition without being toxic to the subject. The selected dosage level will depend on a variety of factors including the activity of the particular compound employed, or salt thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the agents for use within the methods of the presently disclosed subject matter at levels lower than that required to achieve the desired therapeutic effect and gradually increase the dosage until the desired effect is achieved. Accordingly, the dosage range for administration will be adjusted by the physician as necessary. It will be appreciated that an amount of a compound required for achieving the desired biological may be different from the amount of compound effective for another purpose.

In general, a suitable daily dose of an agent for use within the methods of the presently disclosed subject matter will be that amount of the compound that is the lowest dose effective to produce a therapeutic effect. Such an effective dose will generally depend upon the factors described above. Generally, doses of the agents for use within the methods of the presently disclosed subject matter will range from about 0.0001 to about 1000 mg per kilogram of body weight of the subject per day. In certain embodiments, the dosage is between about 1 µg/kg and about 500 mg/kg, more preferably between about 0.01 mg/kg and about 50 mg/kg. For example, in certain embodiments, a dose can be about 1, 5, 10, 15, 20, or 40 mg/kg/day.

If desired, the effective daily dose of an agent for use within the methods of the presently disclosed subject matter can be administered as two, three, four, five, six or more sub-doses administered separately at appropriate intervals throughout the day, optionally, in unit dosage forms.

In some embodiments, the presently disclosed subject matter also provides a method of instructing a subject in need of therapy through the buccal, sublingual or intranasal delivery of fospropofol by providing instructions to receive a treatment comprising a pharmaceutically acceptable composition comprising fospropofol in an amount sufficient to produce a physiologically acceptable effect in the subject. The term "instructing" a subject as used herein means providing directions for applicable therapy, medication, treatment, treatment regimens, and the like, by any means, but preferably in writing. Instructing can be in the form of prescribing a course of treatment, or can be in the form of package inserts or other written promotional material.

In some embodiments, the presently disclosed subject matter provides a method of promoting a treatment for a subject in need of therapy through the buccal, sublingual or intranasal delivery of fospropofol, wherein the treatment comprises a pharmaceutically acceptable composition comprising fospropofol in an amount sufficient to produce a physiologically acceptable effect in the subject. The term "promoting" as used herein means offering, advertising, selling, or describing a particular drug, combination of drugs, or treatment modality, by any means, including writing, such as in the form of package inserts. Promoting herein refers to promotion of treatment regimen including the buccal, sublingual or intranasal delivery of fospropofol, where such promoting is authorized by the Food and Drug Administration (FDA) as having been demonstrated to be associated with statistically significant therapeutic efficacy and acceptable safety in a population of subjects. In some embodiments, promoting is not authorized by the Food and Drug Administration (FDA) (or other health regulatory agency, such as the European Medicines Agency (EMA), and promoting is for an off-label use. In some embodiments, the package insert provides instructions to receive treatment through the buccal, sublingual or intranasal delivery of fospropofol. In some embodiments, the promotion is by a package insert accompanying a formulation comprising the fospropofol composition. In some embodiments, the promotion is by written communication to a physician or health care provider. In some embodiments, the promotion is by oral communication to a physician or health care provider.

In other embodiments, the presently disclosed subject matter provides a pharmaceutical composition for transmucosally administering fospropofol to a subject in need of treatment thereof in an amount sufficient to deliver a therapeutically effective amount of propofol to the subject.

One of skill in the art will recognize that agents for use within the methods of the presently disclosed subject matter include the pharmaceutically acceptable salts of the compounds described above. The term "pharmaceutically acceptable salts" is meant to include salts of active compounds, which are prepared with relatively nontoxic acids or bases, depending on the particular substituent moieties found on the compounds described herein.

When agents for use within the methods of the presently disclosed subject matter contain relatively acidic functionalities, base addition salts can be obtained by contacting the neutral form of such compounds with a sufficient amount of the desired base, either neat or in a suitable inert solvent. Examples of pharmaceutically acceptable base addition salts include alkali or alkaline earth metal salts including, but not limited to, sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

When agents for use within the methods of the presently disclosed subject matter contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids including, but not limited to, hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids, such as acetic (acetates), propionic (propionates), isobutyric (isobutyrates), maleic (maleates), malonic, benzoic (benzoates), succinic (succinates), suberic, fumaric (fumarates), lactic (lactates), mandelic (mandelates), phthalic (phthalates), benzenesulfonic (benzosulfonates), p-tolylsulfonic, citric (citrates), tartaric (tartrates, e.g., (+)-tartrates, (−)-tartrates or mixtures thereof including racemic mixtures), methanesulfonic, and the like. Other pharmaceutically acceptable salts, include, but are not limited to, besylate, bicarbonate, bitartrate, bromide, calcium edetate, carnsylate, carbonate, edetate, edisylate, estolate, esylate, gluceptate, gluconate, glutamate, glycollylarsanilate, hexylresorcinate, hydrabamine, hydroxynaphthoate, iodide, isethionate, lactobionate, malate, mesylate, mucate, napsylate, nitrate, pamoate (embonate), pantothenate, phosphate/diphosphate, polygalacturonate, salicylate, stearate, subacetate, sulfate, tannate, and teoclate, also are included.

Also included are salts of amino acids, such as arginate and the like, and salts of organic acids, such as, glucuronic or galactunoric acids, and the like. See, for example, Berge et al, "Pharmaceutical Salts", Journal of Pharmaceutical Science, 1977, 66, 1-19. Some compounds of the present disclosure can contain both basic and acidic functionalities, which allow the compounds to be converted into either base or acid addition salts.

The neutral forms of the agents for use within the methods of the presently disclosed subject matter may be regenerated by contacting the salt with a base or acid and isolating the parent compound in the conventional manner. The parent form of the compound differs from the various salt forms in certain physical properties. For example, salts tend to be more soluble in aqueous or other protonic solvents than are the corresponding free base forms.

In particular embodiments, the pharmaceutically acceptable salt of an agents for use within the methods of the presently disclosed subject matter is selected from the group consisting of HCl, a sulfonate, a sulfate, phosphate, a malonate, a succinate, a fumarate, a maleate, a tartrate, a 3-sulfopropanoic acid salt, and a citrate. Certain agents for use within the methods of the presently disclosed subject matter can exist in unsolvated forms, as well as solvated forms, including hydrated forms. In general, the solvated forms are equivalent to unsolvated forms and are encompassed within the scope of the present disclosure. Certain agents for use within the methods of the presently disclosed subject matter may exist in multiple crystalline or amorphous forms. In general, all physical forms are equivalent for the uses contemplated by the present disclosure and are intended to be within the scope of the present disclosure.

Methods for the chemical synthesis of the propofol compound of Formula (I) from propofol are described in U.S. Pat. No. 6,204,257 to Stella et al., and are incorporated herein by reference in their entirety. A process for the chemical synthesis of the prodrug is disclosed in international patent application publication WO 03/059255 to Bonneville et al., which is incorporated herein by reference in its entirety. The propofol compound of Formula (I) is water soluble and can be formulated in aqueous solutions or in other suitable pharmaceutical compositions suitable for buccal, sublingual or intranasal administration.

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Gastrointestinal Delivery of Propofol from Fospropofol: Its Bioavailability and Activity in Rodents and Human Volunteers The presently disclosed example investigates, in part, whether the oral bioavailability of propofol from fospropofol might differ from that of propofol due to its novel properties of water solubility and lack of emulsion formulation. In the animal and clinical studies disclosed herein, it is demonstrated that, for the first time, the successful delivery of propofol by administration of the prodrug fosprofol through the gastrointestinal tract, a property that may ultimately be exploited for clinical use.

Overview

In the presently disclosed studies, fospropofol was administered via intravenous, oral and intraduodenal routes to rats. Pharmacokinetic and pharmacodynamic parameters were then evaluated. Based on the promising animal data, an oral and intraduodenal pharmacokinetic/pharmacodynamic study in human volunteers was conducted.

As provided in more detail herein below, in rats, bioavailability of propofol from fospropofol delivered orally was found to be appreciable, in the order of around 20-70%, depending on dose. Availability was especially marked following fospropofol administration via the intraduodenal route, where bioavailability approximated 100%. Fospropofol itself was not appreciably bioavailable when administered by any route except for intravenous. Pharmacologic effect following oral fospropofol was confirmed by observation of sedation and alleviation of thermal hyperalgesia in the rat chronic constrictive injury model of neuropathic pain. The human data also showed systemic availability of propofol from fospropofol administration via oral routes. Assessment of sedation in human volunteers was correlated with pharmacokinetic measurements.

The presently disclosed subject matter provides the utility of oral administration of fospropofol for various therapeutic indications previously considered for propofol.

Methods in Rodent Studies

1. Animal Studies, Drugs and Formulations

Male Sprague-Dawley rats (Charles River, Md., USA) weighing 200-250 g were used, unless otherwise noted. Animals were housed in groups of three-inch suspended polycarbonate cages (18-inches long, 9-inches wide and 9-inches high) under a 12-h light/dark cycle. Food (Harlan/Teklab) and water (filtered and delivered via an automatic watering system) were provided ad libitum. All procedures were conducted in compliance with the laws, regulations and guidelines of the National Institutes of Health (NIH/PHS) and with approval from the local Animal Care and Use committee.

For animal studies, a fospropofol dosing solution was made by dissolving powder in water (for oral and intraduodenal administration) or saline (for intravenous administration) into an administration volume of 1 or 2 mL/kg, as noted.

2. Pharmacokinetic Studies in Rats

Male Sprague-Dawley rats (225-250 g) underwent implantation with indwelling jugular vein catheters for plasma sampling. Animals receiving intravenous (IV) drug administration also underwent femoral vein catheterization and, after full recovery were attached to an electronic infusion pump and administered vehicle or various concentrations of fospropofol in 1 mL total volume by gradual constant rate infusion over 10 min. Intraduodenal (ID)

administration was via previously implanted catheters (HILLTOP Labs, PA) in a constant volume of 2 mL/kg body weight, by slow infusion. Oral administration (PO) was performed via a curved bulb-tipped feeding gavage tube attached to a syringe inserted carefully through the oesophagus via the side of the mouth of manually restrained rats using an administration volume of 1 mL/kg. On the day of testing, control blood samples were taken from the jugular vein prior to dosing of test compounds in conscious rats. In these studies, intravenous doses were based on previously reported behavioral and pharmacokinetic studies with fospropofol. The PO and ID doses were established based on preliminary experiments with behavioral observation, using higher doses based on lower expected oral bioavailability.

After fospropofol administration, blood samples (0.5 mL) were taken at 5, 15, 30, 45, 60, 120, 240 and 360 min post dose. An equivalent volume of blood taken from donor rats of the same strain was administered after each blood sample withdrawal, in an effort to maintain blood volume as previously described (Skrajnar, et al., 2009; Moghaddam, et al., 2002; Choi, et al., 2007). Approximately 0.05 mL of 200 mg/mL of sodium orthovanadate (SOV) solution was added to the heparinized blood collection tubes prior to blood collection to prevent ex vivo conversion via alkaline phosphatases (ALP). The blood samples were mixed, cooled and subsequently centrifuged at 3,000 rpm and 4° C. for 10 min within 30 min of collection. Plasma samples were stored at −20° C. until analysis.

3. Sedative Studies in Rats

The relative potency of fospropofol given via different administration routes was investigated in rats, using sedation as an end point. Intravenous fospropofol doses of 5-40 mg/kg were chosen based on previous studies (Schywalsky, et al., 2003). Based on expected lower oral bioavailability, doses of 100-400 mg/kg were chosen for the PO and ID studies. Following administration of fospropofol, two experimental observers blinded to the treatment, graded the behavior of the rats (n=2-3 per experimental group) every 5 min for a total of 120 min after administration. The scoring system was on a 0-4 scale where 0=alert and completely responsive, 1=alert but less active and 'wobbly', 2=awake but drowsy with periods of inactivity or mild sedation, 3=inactive but readily arousable or moderately sedated, 4=unresponsive, unconscious or deeply sedated. Scores were averaged across treatment groups per time point.

4. Neuropathic Pain Studies in Rats

This study was performed as previously described (Vornov, et al., 2013). In brief, male Sprague-Dawley rats (200-250 g) were anesthetized with halothane. The common sciatic nerve on one hind limb was exposed by separating the biceps femoris from the gluteus superficialis. The nerve was subsequently isolated from the surrounding tissue and four ligatures (4.0 chromic gut) were tied loosely around it with about 1-mm spacing. On the other hind limb of the rat, the nerve was similarly isolated but no ligatures were placed, (sham surgery). Thermal pain sensitivity was evaluated using a plantar test apparatus according to previous methods (Hargreaves, et al., 1988). In brief, this involved applying a constant infrared stimulus to the plantar surface of the hind paw using a Basile Plantar apparatus (Ugo Basile, Vaarese, Italy). Withdrawal latency was measured as the time taken for the rat to withdraw its paw from the heat source to the nearest 0.1 s. The "difference score" was calculated by subtracting the average latency of the non-ligated versus ligated side. Animals were habituated to the test chambers (clear plastic compartment maintained in a quiet room) for several hours over 3-4 days, prior to any measurement.

Baseline hyperalgesia was recorded 10-12 days post-surgery after the habituation. On test day, each animal received either fospropofol (50, 75 or 100 mg/kg) or vehicle (distilled water) via oral gavage in a volume of 2 mL/kg in a randomized and blinded fashion. Withdrawal latency measurements were then recorded five times for both the operated and sham hind paws of each rat starting from 45 to 60 min post dose. The final latency measurement represents a mean of the last four out of a total of five responses, each being taken at least 5 min apart on the same paw. The difference in response latency for each rat for each leg was calculated and used to determine the mean latency difference response time for each group.

Methods in Human Studies

1. Human Studies, Drugs and Formulations

Human studies were approved by the institutional review boards at PRA Health Sciences in Groningen, Netherlands, and were conducted in accordance with the ethical principles that have their origin in the Declaration of Helsinki and the International Conference on Harmonization guideline E6: Good Clinical Practice. All participants provided written, informed consent before study entry and had the right to withdraw from the study at any time.

In human study 1, fospropofol disodium was formulated as a sterile aqueous solution at a concentration of 20 mg/mL. Each vial provided contained 20 mL of solution, suitable for intravenous injection. Fospropofol was administered as a single dose of 400 mg orally, directly into the duodenum by gastroscopy or intravenously over 10 min. In human study 2, fospropofol disodium in capsules (200 mg) or matching placebo was administered orally.

2. Fospropofol Studies in Human Volunteers

The first study was an absolute bioavailability study of fospropofol conducted at a single center (PRA Health Sciences) in Groningen, Netherlands, as a three-way crossover study. The study enrolled 7 healthy male volunteers between 18 and 45 years of age inclusive, with a body mass index between 18 and 28 kg/m$^2$. Subjects stayed in the clinical unit for three consecutive periods of 3 days each, with a 3-day washout, between periods. For six subjects, the order of the administration routes was as follows—period 1: PO, period 2: ID, and period 3: IV. For one subject the order of the administration routes was the following—period 1: ID, period 2: IV and period 3: PO. In this study a single dose of 400 mg was administered by each route. Blinding and placebo control was impractical due to the requirement of unsedated endoscopic administration of fospropofol into the duodenum. Safety and overall pharmacodynamic effect was evaluated based on adverse events, vital signs, electrocardiogram (ECG), Modified Observer's Assessment of Alertness/Sedation (OAA/S) score, clinical laboratory tests, and physical examination.

A second single ascending dose study was subsequently performed to assess the safety, tolerability, and pharmacokinetics of oral administration of fospropofol as a capsule. This was a double-blind, randomized, crossover, placebo-controlled, single ascending dose study. Ten healthy volunteers were enrolled, 6 males and 4 females between 18 and 45 years of age inclusive with a body mass index between 18 and 28 kg/m$^2$. Each subject received four ascending oral doses of fospropofol disodium (200, 600, 1,000 and 1,200 mg) and one of placebo. Placebo was administered randomly, in one of the five periods. Subjects stayed in the clinical research unit over 3 days per treatment for five consecutive treatments. Between treatments, there were wash-out periods of at least 6 days, during which interim safety evaluations were made to assess the safety of the subsequent higher doses. Fopropofol disodium in capsules (200 mg) or matching placebo was administered orally. Pharmacokinetic parameters, safety and pharmacodynamic effect were assessed in a manner similar to that in Study 1 described above. In addition, the digit symbol substitution test (DSST) and BIS Index (a commercially available EEG derived measure of anesthesia and sedation, Coviden, Mansfield, Mass., USA) were added as additional pharmacodynamics measures.

In the first study, 6 mL blood samples were collected following the PO and ID fospropofol treatment periods at times of pre-dose, 5, 10, 20, 30, 45, 60, 90 min and 2, 4, 6 and 9 h post-dose and in the IV fospropofol treatment period at pre-dose and at 5, 10, 15, 20, 30, 45, 60 and 120 min post-dose. In the second study a 6 mL blood sample was collected following each fospropofol PO dose (200, 600, 1,000 and 1,200 mg) at pre-dose, 5, 10, 20, 30, 45, 60, 90 min and 2, 4, 6 and 9 h post-dose. The blood was collected in a sodium heparin vacutainer tube containing 60 mg SOV, inverted approximately eight times to dissolve SOV and placed on dry ice until it was centrifuged at 3,000 rpm for 10 min at 4° C. to harvest plasma. Plasma samples were then stored at −20° C. until analysis.

3. Bioanalysis of Propofol and Fospropofol

Fospropofol and propofol in human and rat plasma were quantified using a validated high performance liquid chromatography (HPLC) with a tandem mass spectrometry method (LC/MS/MS) and an HPLC fluorescence detection method respectively, as described herein below.

For fospropofol analysis, fospropofol-$d_6$ (internal standard prepared in 1.0 M ammonium acetate buffer) was added to the plasma samples (rat or human: 0.05 mL) and subsequently extracted using a solid phase extraction (SPE). The SPE cartridges were conditioned by gravity with methanol and 1.0 M ammonium acetate solution in water. The plasma samples with internal standard were loaded on the cartridges, washed with water and 10% methanol/water and eluted with methanol. The tubes were then evaporated under nitrogen and the residues reconstituted with 50/50 methanol/25 mM ammonium acetate in deionized water. The sample extract was then injected onto a reversed phase HPLC Zorbax Eclipse XDB-C18 column. The separated analytes were detected using tandem mass spectrometry (MS/MS) detection. Fospropofol was quantitated by peak area ratio to its internal standard by mass spectrometry using a selective reaction monitoring mode (for fospropofol m/z=287.1→79.1, and for $D_6$-fospropofol m/z=293.1→79.1). The assays were linear with correlation coefficient of ($R^2$)>0.99 over the range of 10-2,000 ng/mL for rat plasma and 5-1,000 ng/mL for human plasma. Fospropofol was stable for 98 days at −20° C. in rat plasma and 464 days at −20° C. in human plasma.

The propofol plasma assay method was modified from an earlier published method (Plummer, 1987). In brief, 4-[tert-octyl] phenol, (internal standard) was added to the plasma samples (0.05 mL for rat or 0.2 mL for human) and extracted using a 3M Empore C-18-SD 4 mm SPE cartridge (Millipore, Billerica, Mass., USA). A mixture of plasma sample with drug and internal standard in ammonium acetate buffer was passed through the SPE conditioned with methanol and water. The SPE cartridge was further subjected to three wash steps; first with 1 mL of water, second with 1 mL of 10% methanol in water, and third with 20% acetonitrile in water. Finally the analytes were eluted using two times 0.15 mL of acetonitrile. The final eluants (~0.3 mL) were diluted with 0.3 mL of water, and injected onto an HPLC system equipped with a C-18 analytical column (5 μm, 150×3.9 mm) and fluorescence detector set at excitation and emission wave lengths of 275 and 310 nm, respectively. Propofol was quantitated by peak height ratio to internal standard. The assays were linear with correlation coefficient of ($R^2$)>0.99 over the range of 5-2,000 ng/mL for both rat and human plasma. As reported by Shah et al. (Shah, et al., 2008), the precise measurement of plasma propofol using this method may be compromised under conditions of severe hemolysis, as this causes insolubility of the added SOV during sample collection which could result in incomplete ALP inhibition. Given this, hemolysis was avoided or minimized in both the preclinical and clinical studies by conducting sample processing in a cold environment. Propofol was found to be stable at −20° C. for 65 days in rat plasma and 347 days in human plasma. All rat and human study samples in this study were analyzed without exceeding the stability sample integrity during validation of the methods.

4. Pharmacokinetic Parameter Calculations

Pharmacokinetic parameters were determined for fospropofol and propofol from plasma including area under the concentration—time curve from time of dosing to the last measured concentration ($AUC_{(0-t)}$), peak concentration ($C_{max}$), time to reach maximum concentration ($T_{max}$), terminal phase half-life ($t_{1/2}$) and area under the concentration—time curve from time of dosing to infinity ($AUC_{(0-\infty)}$). Absolute bioavailability (F) was calculated as the ratio of AUC(0-∞) resulting from PO or ID administration to AUC (0-∞) following IV administration, correcting for the specific doses used. The parameters were summarized using descriptive statistics.

Results

1. Bioavailability of Fospropofol and Propofol Following IV, PO and ID Dosing of Fospropofol in Rats Following IV, PO and ID administrations the $C_{max}$ and AUC of fospropofol increased with dose (see Table 1 below; FIG. 1A, FIG. 1B, FIG. 1C, and FIG. 1D).

The increase in both parameters, however, was less than dose proportional following IV administration and greater than dose proportional following both PO and ID administrations. The absolute bioavailability of fospropofol was low following both PO and ID administrations, ranging between 0.448 and 3.46% (PO 20 and 100 mg/kg) and 0.264 and 1.03% (ID 30 and 100 mg/kg), respectively.

The $C_{max}$ and AUC of propofol increased with dose. The increase in $C_{max}$ and AUC was dose proportional for IV administration; in contrast, these parameters increased although not dose proportionally, following PO and ID administration (Table 2 below). The propofol bio-availability following fospropofol administration via the PO and ID routes ranged between 22.7 and 70.5% (PO 20 and 100 mg/kg fospropofol) and 47.3-141% (ID 30 and 100 mg/kg fospropofol), respectively.

TABLE 1

Mean (±SD) pharmacokinetic parameters of fospropofol following fospropofol administration in rats

| Route | Dose (mg/kg) | $C_{max}$ (μg/mL) | $AUC_{(0-t)}$ (μg h/mL) | $AUC_{0-\infty}$ (μg h/mL) | $T_{1/2}$ (h) | $V_d$ (L/kg) | $CL_p$ (L/h/kg) | $F^a$ (%) |
|---|---|---|---|---|---|---|---|---|
| IV | 5 | 16.3 (±1.80) | 3.15 (±0.29) | 3.15 (±0.28) | 0.49 (±0.28) | 1.02 (±0.66) | 1.38 (±0.125) | — |
| PO | 20 | 0.23 (±0.07) | 0.05 (±0.008) | 0.06 (±0.007) | 0.19 (±0.27) | — | — | 0.448 |
| PO | 100 | 9.23 (±4.09) | 2.16 (±0.99) | 2.18 (±0.99) | 0.49 (±0.24) | — | — | 3.46 |
| ID | 30 | $0.17^b$ | 0.044 | 0.05 | 0.21 nd | — | — | 0.264 |
| ID | 100 | 3.74 (±2.12) | 0.644 (±0.38) | 0.65 (±0.39) | 0.23 (±0.1) | — | — | 1.03 | nd not determined as only one rat showed terminal elimination.
[a] Ratio of mean of $AUC_{(0-\infty)}$ to reference treatment of 5 mg/kg IV fospropofol.
[b] N + 1

TABLE 2

Mean (±SD) pharmacokinetic parameters of propofol following fospropofol administration in rats

| Route | Dose (mg/kg) | $C_{max}$ (μg/mL) | $AUC_{0-t}$ (μg h/mL) | $AUC_{0-\infty}$ (μg h/mL) | $T_{1/2}$ (h) | F a (%) |
|---|---|---|---|---|---|---|
| IV | 5 | 0.29 (±0.04) | 0.12 (±0.02) | 0.14 (±0.03) | ND | ND |
| PO | 20 | 0.04 (±0.001) | 0.06 (±0.04) | 0.13 (±0.12) | 4.66 (±4.13) | 22.7 |
| PO | 100 | 0.53 (±0.08) | 1.21 (±0.2) | 1.96 (±0.6) | 4.13 (±1.12) | 70.5 |
| ID | 30 | 1.27 (±0.87) | 0.353 (±0.14) | 0.398 (±0.14) | 2.85 (±0.87) | 47.3 |
| ID | 100 | 5.84 (±2.29) | 3.57 (±0.57) | 3.95 (±0.48) | 2.32 (±0.73) | 141 | a Ratio of mean of $AUC_{(0-\infty)}$ to reference treatment of 5 mg/kg IV fospropofol 2. Sedative Effects of PO and ID Administration of Fospropofol in Rats Intravenous administration of fospropofol rapidly induced a dose-related sedation at 10-40 mg/kg (FIG. 2A). The sedative effects were evident within 1 min and abated within 30 min after infusion.

After PO administration, animals displayed a rapid (within 5-10 min of dosing) dose-dependent onset of sedated behavior, followed quickly by loss of consciousness in the 300 and 400 mg/kg groups (FIG. 2B), which lasted for up to approximately 1 h. Rats in the intermediate PO dose groups (100-200 mg/kg) displayed signs of mild to moderate sedation lasting about 1-2 h. In general, onset of sedation was slower and of longer duration after PO administration compared to the IV route (FIG. 2A).

Similar to IV administration, ID fospropofol resulted in a similar rapid onset of sedation (within 5 min of its administration), followed by loss of consciousness in the higher dose groups. The onset of sedation was slightly faster than after PO administration and required lower doses (similar to those associated with the IV route) for the same maximal effect (FIG. 2A and FIG. 2C). The duration of effect after ID administration was shorter than after PO administration at these lower doses, generally consistent with the time course predicted by pharmacokinetics.

3. Analgesic Effects of PO Fospropofol Administration in Rats

Fospropofol was active in alleviating thermal hyperalgesia in the rat chronic constrictive injury model of neuropathic pain at doses of 75 and 100 mg/kg PO, but not at 50 mg/kg (FIG. 3A). These effects were not due to general sedative effects as reflected by no change in latencies of response to stimuli on the sham (non-ligated side) in fospropofol treated rats vs vehicle (FIG. 3B). In a separate study, rats (n=10 per group) were dosed with fospropofol PO at 75 mg/kg in a volume of 2 mL/kg. Withdrawal latency was then tested at different time points following dosing (1, 2 and 4 h). Fospropofol was effective only when tested at 1 h after administration and not after longer time periods (data not shown). Mean absolute latencies of ipsilateral paw before and after fospropofol or vehicle treatment are shown in FIG. 6.

4. Bioavailability of Fospropofol and Propofol in Human Volunteers Following PO and ID Fospropofol Study 1 In this three-way crossover study, absorption of fospropofol was rapid following PO and ID administrations, with $T_{max}$ of 0.08 and 0.17 h, respectively. The mean plasma concentrations of fospropofol declined rapidly after reaching $C_{max}$ (FIG. 4A). Compared with IV fospropofol administration, the PO and ID fospropofol resulted in extremely low mean plasma concentrations of fospropofol. Compared with the $C_{max}$ of IV fospropofol, the PO and ID Cmax values were approximately 88- and 534-fold lower, respectively (data not shown). The absolute bioavailability of fospropofol after PO and ID administration was very low (1% for PO and 0.1% for ID administration). The mean $t_{1/2}$ of fospropofol was similar following all methods of delivery (0.32, 0.28, and 0.28 h for PO, ID and IV, respectively).

Compared with the $C_{max}$ of propofol after IV administration of fospropofol, the $C_{max}$ values after PO and ID administration were approximately five and three-fold lower, respectively. The bioavailability (F), based on AUC(0-∞), of propofol was 30% for oral administration and 37% for ID administration. The liberation and appearance of propofol from fospropofol in systemic circulation was rapid following ID and PO administrations with $T_{max}$ of 0.17 and 0.33 h, respectively. The $t_{1/2}$ and $T_{max}$ for propofol tended to be longer after PO administration than it was following ID and IV administrations (FIG. 4B).

Study 2 In this oral dose escalation study, fospropofol and propofol exposure showed dose related increase following PO doses of fospropofol in capsule form (FIG. 5A, FIG. 5B, FIG. 5C, and FIG. 5D).

5. Safety and Tolerability of PO and ID Fospropofol in Human

Study 1 Seventy-three treatment emergent adverse events (TEAEs) were reported in 7 of 7 subjects (100%), (and are detailed in Table 3 below). Seventy of the reported TEAEs were considered to be possibly or probably related to the study drug. The most frequently reported TEAEs were somnolence [11 events in 7/7 subjects (100%)], paresthesia [10 events in 6/7 subjects (86%)], speech disorder [6 events in 6/7 subjects (86%)], and burning sensation [6 events in 3/7 subjects (43%)]. Two subjects (29%), one in the PO group and one in the IV group, reported one TEAE each of euphoria. Both events were mild, considered related to study medication and resolved after 17 and 34 min, respectively. No subject experienced a serious adverse event (SAE) and no subject discontinued from the study for any reason. These results are detailed in Table 3.

There was a marked difference in the number of treatment-related TEAEs reported among the different routes of administration. When fospropofol was administered IV, 7 of 7 (100%) subjects reported 56 treatment-related TEAEs. When fospropofol was administered either PO or ID, 6 of 7 (86%) subjects in each group reported 8 and 9 treatment-related TEAEs, respectively. No severe or serious TEAEs were reported during this study. There was no death or study discontinuation because of an AE. All but one TEAE (rash, which resolved without treatment) resolved without sequelae within 1 h of dosing. The Investigator considered all TEAEs mild. No clinically-relevant abnormalities were found with regard to clinical laboratory results, vital signs, ECG, or physical examination.

The Modified OAA/S scale was used to assess subjects' level of sedation. The lowest observed Modified OAA/S

TABLE 3

Frequency table of all treatment-emergent adverse events from Study 1

| Treatment-emergent Adverse Events System organ class/preferred Term | Total (N = 7) E n (%) | T1: PO (N = 7) E n (%) | T2: ID (N = 7) E n (%) | R: IV N = 7 E n (%) |
|---|---|---|---|---|
| BLOOD AND LYMPHATIC SYSTEM DISORDERS | 1 1 (14%) | | | 1 1 (14%) |
| lymph node pain | 1 1 (14%) | | | 1 1 (14%) |
| EYE DISORDERS | 5 5 (71%) | | | 5 5 (71%) |
| diplopia | 1 1 (14%) | | | 1 1 (14%) |
| visual disturbance | 4 4 (57%) | | | 4 4 (54%) |
| GASTROINTESTINAL DISORDERS | 6 4 (57%) | 1 1 (14%) | 1 1 (14%) | 4 3 (43%) |
| dry mouth | 1 1 (14%) | | | 1 1 (14%) |
| dyspepsia | 1 1 (14%) | | | 1 1 (14%) |
| flatulence | 1 1 (14%) | | 1 1 (14%) | |
| nausea | 2 1 (14%) | 1 1 (14%) | | 1 1 (14%) |
| proctalgia | 1 1 (14%) | | | 1 1 (14%) |
| GENERAL DISORDERS AND ADMINISTRATION SITE CONDITIONS | 12 5 (71%) | | 3 3 (43%) | 9 4 (57%) |
| catheter site pain | 1 1 (14%) | | | 1 1 (14%) |
| fatigue | 4 3 (43%) | | 2 2 (29%) | 2 2 (29%) |
| feeling abnormal | 1 1 (14%) | | | 1 1 (14%) |
| feeling cold | 1 1 (14%) | | | 1 1 (14%) |
| feeling drunk | 1 1 (14%) | | | 1 1 (14%) |
| sluggishness | 3 3 (43%) | | | 3 3 (43%) |
| subrapubic pain | 1 1 (14%) | | 1 1 (14%) | |
| INFECTIONS AND INFESTATIONS | 1 1 (14%) | | 1 1 (14%) | |
| herpes simplex | 1 1 (14%) | | 1 1 (14%) | |
| MUSCULOSKELETAL AND CONNECTIVE TISSUE DISORDERS | 2 2 (29%) | | | 2 2 (29%) |
| muscle fatigue | 2 2 (29%) | | | 2 2 (29%) |
| NERVOUS SYSTEM DISORDERS | 40 7 (100%) | 6 4 (57%) | 3 3 (43%) | 31 7 (100%) |
| burning sensation | 6 3 (43%) | | | 6 3 (43%) |
| dizziness | 5 3 (43%) | 1 1 (14%) | 1 1 (14%) | 3 3 (43%) |
| dizziness postural | 1 1 (14%) | | | 1 1 (14%) |
| paresthesia | 10 6 (86%) | 1 1 (14%) | | 9 6 (86%) |
| somnolence | 11 7 (100%) | 4 4 (57%) | 2 2 (29%) | 5 5 (71%) |
| speech disorder | 6 6 (86%) | | | 6 6 (86%) |
| tremor | 1 1 (14%) | | | 1 1 (14%) |
| PSYCHIATRIC DISORDERS | 3 3 (43%) | 1 1 (14%) | | 2 2 (29%) |
| disorientation | 1 1 (14%) | | | 1 1 (14%) |
| euphoric mood | 2 2 (29%) | 1 1 (14%) | | 1 1 (14%) |
| REPRODUCTVE SYSTEM AND BREAST DISORDERS | 1 1 (14%) | | | 1 1 (14%) |
| genital pruritis male | 1 1 (14%) | | | 1 1 (14%) |
| SKIN AND SUBCUTANEOUS TISSUE DISORDERS | 2 2 (29%) | | 1 1 (14%) | 1 1 (14%) |
| ecchymosis | 1 1 (14%) | | | 1 1 (14%) |
| rash | 1 1 (14%) | | 1 1 (14%) | |
| TOTAL | 73 7 (100%) | 8 6 (86%) | 9 6 (86%) | 56 7 (100%) |

N: number of subjects exposed
E: number of adverse events
n (%): number and percentage of subjects with adverse events
Note:
Each occurrence, independent of whether it may be the same adverse event in the same subject during one treatment was counted score during this study was 4 (responded lethargically to name spoken in normal tone). Three of 7 (43%) and 4 of 7 (57%) subjects in the ID and IV groups respectively, had a Modified OAA/S score of 4 at some time following drug administration. All other subjects in those treatment groups and all subjects in the oral treatment group responded readily to their name spoken in normal tone (Modified OAA/S score of 5) at all times. All subjects had Modified OAA/S scores of 5 by 1.5 h postdose. This observation of similar sedation levels produced by IV and ID administration compared to PO administration are generally consistent with the pharmacokinetic measurements that suggested somewhat higher duodenal than oral bioavailability.

Study 2 The patient incidence of TEAEs by treatment was: 40, 80, 90, 80, and 90% for placebo, 200, 600, 1,000, and 1,200 mg, respectively. (These are detailed in Table 4 below). Somnolence was reported in 0, 40, 50, 40, and 80% of subjects in the placebo, 200, 600, 1,000, and 1,200 mg groups, respectively. Following somnolence in rate of occurrence were paresthesia (60%), nausea (50%), and phlebitis superficial (50%). Most of the TEAEs were mild or moderate in severity and resolved without intervention. Two subjects (1 in the 1,000 mg treatment group and 1 in the 1,200 mg group) experienced somnolence that was considered severe by the Investigator. Only one TEAE (erythema in the placebo group, considered not related to study drug) required treatment and resolved before the end of the study. Euphoric mood was reported as a TEAE in three subjects during this study; one each in the placebo, 600, and 1,200 mg groups. There were no changes in laboratory values, vital signs, ECGs, or physical examinations that were considered clinically relevant by the Investigator during this study. No subject experienced a SAE and no subject discontinued from the study for any reason.

At most time points ≥80% of subjects in each of the treatment groups responded readily to their names spoken in a normal tone (Modified OAA/S scores of 5).

At the 1.5-h time point in the 1,200 mg treatment group, however, 40% of subjects had a Modified OAA/S score of 4 (responded lethargically to their names spoken in a normal tone). The lowest Modified OAA/S scores (score of 3; responded only after name was called loudly and/or repeatedly) were recorded by the same subject (Subject 003, following treatment with 1,000 mg), at 1 and 1.5 h after treatment with fospropofol disodium.

DSST (digital symbol substitution test) performance decreased in a dose dependent manner. The maximal DSST changes from baseline for all fospropofol disodium treatment groups were recorded at the 1-h time point. At 1 h post-treatment, mean changes were 6, −5, −11, and −13 for the 200, 600, 1,000, and 1,200 mg groups, respectively. The BIS (bispectral index score), however, was not affected by fospropofol administration at any dose level where mean BIS scores were >90% at all the time points for all subjects following all treatments. Ranges were 67-98%, 80-98%, 71-98%, 70-98%, and 70-98% for the placebo, 200, 600, 1,000, and 1,200 mg groups, respectively.

TABLE 4

Frequency table of all treatment - emergent adverse events in Study 2, by system organ class and preferred terminology (number of events and number of subjects).

| Treatment-emergent Adverse Events System organ Class/preferred term | Total (N = 10) E n (5%) | Placebo (N = 10) E n (%) | 200 mg Fospropofol (N = 10) E n (%) | 600 mg Fospropofol (N = 10) E n (%) | 1000 mg Fospropofol (N = 10) E n (%) | 1200 mg Fospropofol (N = 10) E n (%) |
|---|---|---|---|---|---|---|
| CARDIAC DISORDERS | 1 1 (10%) | | | | | 1 1 (10%) |
| palpitations | 1 1 (10%) | | | | | 1 1 (10%) |
| EYE DISORDERS | 2 2 (20%) | 1 1 (10%) | 1 1 (10%) | | | |
| eye irritation | 1 1 (10%) | | 1 1 (10%) | | | |
| eye pain | 1 1 (10%) | 1 1 (10%) | | | | |
| GASTROINTESTINAL DISORDERS | 13 8 (80%) | | 2 1 (10%) | 4 3 (30%) | 4 4 (40%) | 3 3 (30%) |
| abdominal pain | 2 2 (20%) | | 1 1 (10%) | 1 1 (10%) | | |
| bowel sounds abnormal | 1 1 (10%) | | | 1 1 (10%) | | |
| defecation urgency | 1 1 (10%) | | | | | 1 1 (10%) |
| dysphagia | 1 1 (10%) | | | | 1 1 (10%) | |
| nausea | 7 5 (50%) | | 1 1 (10%) | 1 1 (10%) | 3 3 (30%) | 2 2 (20%) |
| proctalgia | 1 1 (10%) | | | 1 1 (10%) | | |
| GENERAL DISORDERS AND ADMINISTRATION SITE CONDITIONS | 15 4 (40%) | | 1 1 (10%) | 5 4 (40%) | 3 3 (30%) | 6 3 (30%) |
| fatigue | 4 2 (20%) | | | 2 2 (20%) | 1 1 (10%) | 1 1 (10%) |
| feeling hot | 10 4 (40%) | | 1 1 (10%) | 3 3 (30%) | 2 2 (20%) | 4 3 (30%) |
| malaise | 1 1 (10%) | | | | | |

TABLE 4-continued

Frequency table of all treatment - emergent adverse events in Study 2, by system organ class and preferred terminology (number of events and number of subjects).

| Treatment-emergent Adverse Events System organ Class/preferred term | Total (N = 10) E n (%) | Placebo (N = 10) E n (%) | 200 mg Fospropofol (N = 10) E n (%) | 600 mg Fospropofol (N = 10) E n (%) | 1000 mg Fospropofol (N = 10) E n (%) | 1200 mg Fospropofol (N = 10) E n (%) |
|---|---|---|---|---|---|---|
| INFECTIONS AND INFESTATIONS | 2 2 (20%) | 1 1 (10%) | 1 1 (10%) | | | 1 1 (14%) |
| rhinitis | 2 2 (20%) | 1 1 (10%) | 1 1 (10%) | | | |
| MUSCULOSKELETAL AND CONNECTIVE DISORDERS | 1 1 (20%) | | | 1 1 (10%) | | |
| sensation of heaviness | 1 1 (10%) | | | 1 1 (10%) | | |
| NERVOUS SYSTEM DISORDERS | 53 10 (100%) | | 10 7 (70%) | 16 7 (70%) | 14 7 (70%) | 13 9 (90%) |
| dizziness | 2 2 (20%) | | | 2 2 (20%) | | |
| dysgeusia | 1 1 (10%) | | | 1 1 (10%) | | |
| headache | 9 3 (30%) | | | 3 2 (20%) | 2 2 (20%) | 1 1 (10%) |
| paraesthesia | 18 6 (60%) | | 3 2 (20%) | 5 5 (50%) | 7 6 (60%) | 3 3 (30%) |
| paraesthesia oral | 2 1 (10%) | | 3 3 (30%) | | 1 1 (10%) | 1 1 (10%) |
| somnolence | 21 10 (100%) | | 4 4 (10%) | 5 5 (50%) | 4 4 (40%) | 8 8 (80%) |
| PSYCHIATRIC DISORDERS | 3 3 (30%) | 1 1 (10%) | | 1 1 (10%) | | 1 1 (10%) |
| euphoric mood | 3 3 (30%) | 1 1 (10%) | | 1 1 (10%) | | 1 1 (10%) |
| REPRODUCTIVE SYSTEM AND BREAST DISORDERS | 3 1 (10%) | | | 1 1 (10%) | 1 1 (10%) | 1 1 (10%) |
| perineal pain | 3 1 (10%) | | | 1 1 (10%) | 1 1 (10%) | 1 1 (10%) |
| RESPIRATORY THORACIC AND MEDIASTINAL DISORDERS | 5 4 (40%) | 1 1 (10%) | 1 1 (10%) | 1 1 (10%) | 1 1 (10%) | 1 1 (10%) |
| dyspnoea | 1 1 (10%) | | | | | 1 1 (10%) |
| pharyngolaryngeal pain | 3 3 (30%) | 1 1 (10%) | 1 1 (10%) | 1 1 (10%) | | |
| throat irritation | 1 1 (10%) | | | | 1 1 (10%) | |
| SKIN AND SUBCUTANEOUS TISSUE DISORDERS | 1 1 (10%) | 1 1 (10%) | | | | |
| erythema | 1 1 (10%) | 1 1 (10%) | | | | |
| VASCULAR DISORDERS | 9 6 (60%) | 2 2 (20%) | 1 1 (10%) | 1 1 (10%) | 4 3 (30%) | 1 1 (10%) |
| phlebitis superficial | 6 5 (50%) | 1 1 (10%) | | 1 1 (10%) | 4 3 (30%) | |
| vein pain | 3 2 (20%) | 1 1 (10%) | 1 1 (10%) | | | 1 1 (10%) |
| TOTAL | 108 10 (100%) | 7 4 (40%) | 18 8 (80%) | 29 9 (90%) | 28 8 (80%) | 26 9 (90%) |

N: number of subjects exposed
E: number of adverse events
n (%): number and percentage of subjects with adverse events
Note:
Each occurrence, independent of whether it may be the same adverse event in the same subject during one treatment was counted Discussion These results demonstrate for the first time that the water soluble prodrug fospropofol can be used to provide oral bioavailability of propofol in both rat and human. Previous reports concluded that propofol itself has little or no oral bioavailability, presumably due to first pass hepatic metabolism based upon liver extraction of 80% after intravenous administration of lipid emulsion in animals (Cozanitis, et al., 1991; Raoof, et al., 1996; Ceriana, et al., 1996) and in human Hiraoka, et al., 2005; Hiraoka, et al., 2004). In contrast, the presently disclosed subject matter demonstrated that PO and ID fospropofol administration can achieve bioavailability of 30% or more. Interestingly, while propofol availability derived from the prodrug is appreciable; the bioavailability of the prodrug itself is low, suggesting that propofol is liberated from prodrug before entering the central compartment. This observation suggests that prodrug delivery allows propofol in the portal circulation to avoid first pass metabolism by the liver. GI administration resulted in a delayed, lower $C_{max}$ compared to intravenous propofol or fospropofol, but was able to achieve plasma concentrations associated with sedation or analgesia for an hour or more after a single administration. These results suggest for the first time that oral administration of its prodrug may allow safe and practical administration of propofol at subhypnotic exposures for use in treatment of migraine, anxiety or other disease states.

Further, the presently disclosed subject matter shows that bioavailability and sedative effect varied by dose and location of administration in the GI tract of the rat. On a dose basis, fospropofol induced full sedation (an average score of 3.5 or higher, according to the 0-4 rating scale described hereinabove in the "Methods" section, for at least two consecutive recording times) when administered IV at a dose of 40 mg/kg. PO administration produced full sedation scores at 300-400 mg/kg, but only 50 mg/kg was required when administered ID. The time to reach effect and duration was similar through IV or ID routes, but slightly slower in onset and more prolonged following the larger doses required to reach sedation after oral administration, although comparable doses were not administered by both ID and PO routes. This suggests that, at least in rats, either the mechanism by which propofol liberated from fospropofol is dependent in part on the properties of the GI tract or that the conditions in the stomach may partially hydrolyze the prodrug to propofol in the lumen, rendering the propofol unavailable for absorption.

Measurement of plasma propofol in rats confirmed the greater bioavailability of ID compared to PO administration. Interestingly, bioavailability of fospropofol was consistently low when administered at either site in the GI tract, suggesting that the prodrug is hydrolyzed to release propofol prior to reaching the central compartment. Relative propofol bioavailability rose with PO or ID doses, reaching 70% or more at the highest doses administered. The difference in dose required by the PO route to achieve sedation appeared to be due largely to the lower $C_{max}$ even as propofol bioavailability increased on an AUC basis. The higher $C_{max}$ for the ID route corresponded to a lower required dose for full sedation.

While food effect was not formally studied, it should be noted that all pharmacokinetic and sedative animal studies were conducted in the fasted state, whereas the neuropathic pain studies were undertaken in rats with free access to food. It is likely that fospropofol would be deemed a class 1 drug under the Biopharmaceutics Classification System, due its high permeability and solubility, so that a food effect would not be expected. Future clinical development of fospropofol through the oral route, however, would require a specific study of food effects.

The clinical observations described herein provide supporting evidence that fospropofol is bioavailable through the GI tract, as well. Dose dependent sedative effects were observed in volunteers administered fospropofol orally by capsule in a dose response study.

The human pharmacokinetic data differed somewhat from rat, suggesting more equal bioavailability from PO and ID administration routes and less dose dependence of bioavailability. There was lower bioavailability, however, from capsules and significant variability in $C_{max}$, suggesting that a food effect may be likely and that a formulation providing predictable blood levels would be desirable, especially given the potentially narrow therapeutic window of propofol.

The bioavailability of fosproprofol through the GI tract is in marked contrast to the lack of bioavailability reported for propofol administered orally to rats and man in an oil/water emulsion formulation, rectally as an oil or in its pure form in soft gelatin capsules (Cozanitis, et al., 1991; Raoof, et al., 1996; Ceriana, et al., 1996). This observation has been explained in part by the high extraction of propofol by the liver in animals and man after intravenous administration in an emulsion. Importantly, it has been shown that propofol can be absorbed buccally when administered in a semifluorinated alkane based formulation (Tsagogiorgas, et al., 2013) supporting the notion that liver metabolism likely limits oral bioavailability of propofol as oil in emulsion. Raoof et al. (Raoof, et al., 1996) studied the relative contribution of intestinal mucosa, liver and lung to in vivo disposition in the rat. In this study, AUC's of propofol were estimated and fractions of the administered dose escaping first pass metabolism by the gut wall (fa), liver (fh) and lung (fl) were calculated using propofol concentration following intra-arterial, intravenous, hepatic portal and oral routes of propofol administration. It was observed that the intestinal mucosa is the main site of first pass metabolism following oral administration of propofol in the rat. The liver and lung contribute much less compared to intestinal mucosa. Intestinal metabolism could therefore also contribute to the systemic clearance of propofol. Due to first pass effect the observed bioavailability of propofol was low (10%).

The oral bioavailability of any drug may be limited by its aqueous solubility, low permeability, propensity to be an efflux substrate, and rapid and extensive hepatic metabolism and biliary excretion. Raoof et al. (Raoof, et al., 1996) also reported that propofol is a highly permeable drug (evaluated using Caco-2 cell monolayers) and known to be a poorly soluble drug. Therefore it can be classified as a biopharmaceutical class (BCS) class II drug. The oral bioavailability of this class of compounds is limited by solubility and not permeability. The presently disclosed data are consistent with the fact that the propofol bioavailability is markedly higher following PO and ID administration of prodrug fospropofol due to its solubility. The absorbed fospropofol rapidly converts to propofol by alkaline phosphatase present in different organs including blood and liver. The low levels of fospropofol following PO administration further support this. Once propofol is in systemic circulation then its disposition is similar to that following IV administration.

The presently disclosed data suggest that the prodrug is hydrolyzed at the gut wall or in the liver, liberating propofol into the central compartment since the prodrug is not seen at appreciable concentrations in the central compartment after oral administration. Without wishing to be bound to any one particular theory, it is assumed that hydrolysis does not occur in the lumen of the gut, since that would result in very low bioavailability like that of propofol. It is unlikely, based on the physiochemical properties of the phosphono-O-methyl prodrug, that fospropofol is absorbed across the gut wall to be hydrolyzed in the portal vein or liver. Therefore, it is most likely that hydrolysis takes place at the gut wall and propofol is delivered as free propofol into the portal vein.

This leaves the question of why propofol liberated from the prodrug at the gut wall is handled differently from propofol in emulsion. Propofol is known to be highly bound to serum proteins, particularly albumin (Schywalsky, et al., 2005). It is therefore likely that propofol is cleaved at the gut wall and then rapidly diffuses to bind to plasma proteins. As a highly bound drug, extraction by the liver may be limited. The dose dependent increase in bioavailability is consistent with observations that free propofol fraction is higher at low plasma propofol concentrations, thus enhancing clearance at low doses compared to higher doses where the free fraction is lower.

Again, without wishing to be bound to any one particular theory, it is thought that the low bioavailability of propofol administered orally or rectally as an emulsion or pure oil is due to propofol binding to plasma lipoproteins that facilitate its active uptake by the liver and subsequent metabolism. It has been shown that formulation has a significant effect on propofol distribution after intravenous administration with the emulsion formulation enhancing rapid brain effect and preventing pulmonary distribution (Tsagogiorgas, et al., 2013; Dutta, et al., 1998; Dutta, et al., 1997). While propofol distribution and metabolism has been extensively studied in many species and in clinical settings, major gaps remain in an understanding of its metabolism. For example, despite the high extraction ratio of propofol by the liver, during liver transplant only minor changes in propofol plasma concentration are observed, even as this major metabolic site is removed during the anhepatic phase. Physiological based modeling efforts have been attempted based on blood flow and tissue metabolism, but fail to predict clinical data and require adjustments to match clinical observations. It may be that intravenous infusion of propofol as emulsion also is influenced by factors such as lipoprotein vs albumin binding that constitute distinct and time varying pools of propofol that are not present when propofol is liberated from a water soluble prodrug. These considerations suggest that more detailed metabolic investigation comparing prodrug to emulsion might prove interesting, including measures of liver extraction of propofol from prodrug compared to emulsion when administered intravenously and through the gastrointestinal tract.

The oral bioavailability was sufficient to show analgesic effects in a rodent neuropathic pain model. Nonsedative doses of 75 or 100 mg/kg were effective after a single dose consistent with achieving plasma concentrations greater than 200 ng/mL. Effects were of short duration, losing activity by 2 h after administration, consistent with the pharmacokinetic profile. These observations are consistent with previous reports of analgesic properties of intrathecal propofol in some acute pain models (e.g., phases 1 and 2 of formalin pain, hotplate and acetic acid writhing), but not in others (tail-flick test) (Nishiyama, et al., 2004; Xu, et al., 2004), and clinical observations of analgesic properties (Zacny, et al., 1996). The demonstration of pharmacologic activity consistent with plasma concentrations confirms that propofol measured in the plasma is fully biologically active. It should be noted that recent publications have shown that environmental enrichment can reduce pain perception in rats (Tall, 2009; Rossi, et al., 2008). The animals in this study, however, were not provided environmental enrichment. Future studies should monitor and compare the analgesic efficacy of propofol with and without enriching conditions.

The analgesic activity of propofol is consistent with its effects as a modulator of gamma-aminobutyric acid (GABA A) neurotransmission, in the spinal cord, as well as the central nervous system (Dong, et al., 2002). Specifically, the effects of propofol on GABA A receptor mediated presynaptic inhibition at primary afferent terminals in the human spinal cord (Shimizu, et al., 2002) are thought to decrease spinal nociception (Jewett, et al., 1992). The reported clinical effects of propofol on migraine and nausea may also be through GABAergic modulatory effects, although the definitive pathways have not been clearly described. Classical benzodiazepines that enhance GABA neurotransmission are not recommended as first line therapy for chronic pain because of CNS side effects and potential worsening of pain syndromes with prolonged use. It is possible however, that propofol's analgesic effects may be mediated through additional mechanisms, such as glutamatergic transmission, sodium channel blockade and NMDA/AMPA receptors (Xu, et al., 2004; Ratnakumari, et al., 1997). A recent publication (Tibbs, et al., 2013) suggests that HCN (hyperpolarization activated, cyclic nucleotide regulated) channels may also mediate effects of propofol in neuropathic pain models. Regardless of the precise mechanism, the clinical utility of propofol oral administration as the prodrug would require longer clinical trials to ensure durable benefit with good tolerability.

The presently disclosed results suggest that the ability to deliver propofol through non-intravenous routes could enable therapeutic utility of this broad pharmacology. Clinical experience and a number of trials provide substantial evidence of propofol's clinical usefulness for treatment of epilepsy, pain, nausea and migraine headache. The presently disclosed studies establish for the first time that, when administered as fospropofol, propofol is orally bioavailable in human volunteers. Finally, in a well validated animal model of neuropathic pain, analgesic effects can be demonstrated by oral administration.

SUMMARY

Propofol is a widely used anesthetic/sedative agent whose diverse pharmacology has shown utility in several clinical conditions including treatment of migraine, nausea, pain and anxiety. Its physical properties, however, including limited solubility and negligible bioavailability via non-intravenous routes, have impeded its more widespread use. The presently disclosed subject matter shows that oral administration of the fospropofol prodrug provides appreciable propofol bioavailability in both animal and in human volunteers. Furthermore, the pharmacological efficacy of oral fospropofol in animal models is demonstrated. These data suggest utility of oral administration of fospropofol for various therapeutic indications previously considered for propofol.

Example 2

Intranasal Delivery of Fospropofol in Monkeys

In this example, the presently disclosed subject matter demonstrates that intranasal administration of fospropofol in rats unexpectedly led to appreciable plasma concentrations of fospropofol in the plasma, unlike oral administration in which only propofol was found in plasma without the prodrug, resembling intravenous administration more that oral administration. Uniquely however, propofol was found in the brain at higher concentrations than plasma propofol, suggesting direct entry of prodrug into the brain with direct delivery of propofol to the brain.

In monkeys, this finding was confirmed in part by demonstrating that intranasal administration is followed by appreciable plasma concentrations of prodrug, reproducing the observation made in rats. Surprisingly, buccal administration in monkeys showed a unique profile in plasma with transient appearance of fospropofol, peaking between 30 and 60 minutes after administration, accompanied by a gradual increase in propofol concentration rising through the 120 min of observation.

Without wishing to be bound to any one particular theory, it appears that buccal administration of fospropofol provides a method of controlled, sustained delivery of propofol by delivering free propofol to plasma and avoiding first pass liver metabolism.

In summary, the nasal and buccal administration routes each provide unique exposure profiles ideal for treatment of a variety of neurological and psychiatric conditions. Intranasal administration provides rapid delivery of propofol to brain, useful in the most acute disorders such as epilepsy, while buccal administration provides controlled, sustained administration where high peaks and resulting sedation is to be avoided.

More particularly, in this example, monkeys were dosed with 50 mg fospropofol by intranasal administration. Plasma and cerebrospinal fluid (CSF) were collected before treatment (graphed as t=0), 15 minutes, 30 minutes, 1 hr, and 2 hr. Samples were analyzed for propofol and fospropofol by LC/MS. Propofol was not quantifiable in any of the plasma samples. Only two of the CSF samples showed fospropofol in the low nanomolar range. These samples are near the limit of quantification. FIGS. 11A and 11B show the data in nM and ng/mL scales, respectively.

Example 3

Buccal Delivery of Fospropofol in Monkeys

In this example, monkeys were dosed with 50 mg fospropofol by buccal administration. Plasma and CSF were collected before treatment (graphed as t=0), 15 minutes, 30 minutes, 1 hr and 2 hr. Samples were analyzed for propofol and fospropofol by LCMS.

In plasma, fospropofol peaks around 30-60 minutes with a $C_{max}$ around 150 nM and goes below the limit of quantification by 2 hr. Conversion to propofol causes propofol plasma levels to increase over the course of the experiment with the highest levels in plasma at about 500 nM at 2 hours (see FIGS. 12A and 12B). Referring now to FIGS. 13A and 13B, CSF fospropofol levels are similar to plasma levels with the exception of one high point (at approximately 850 nM) at 15 minutes. Fospropofol does not seem to readily convert to propofol in the CSF so only 2 samples are above the limit of quantitation of 10 nM.

REFERENCES

All publications, patent applications, patents, and other references mentioned in the specification are indicative of the level of those skilled in the art to which the presently disclosed subject matter pertains. All publications, patent applications, patents, and other references (e.g., websites, databases, etc.) mentioned in the specification are herein incorporated by reference in their entirety to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

Borgeat A, Wilder-Smith O, Mentha G, Huber O (1992) Propofol and cholestatic pruritus. Am J Gastroenterol 87:672-674.

Borgeat A, Wilder-Smith O H, Mentha G (1993) Subhypnotic doses of propofol relieve pruritus associated with liver disease. Gastroenterology 104:244-247.

Borgeat A, Wilder-Smith O H, Suter P M (1994) The nonhypnotic therapeutic applications of propofol. Anesthesiology 80:642-656.

Ceriana R, Braschi A, De Ponti F, Crema A, De Amici D (1996) Is rectal administration of propofol effective? Anaesthesia 51:504.

Choi Y H, Bae S K, Oh J M, Kim S O, Lee M G (2007) Pharmacokinetics of intravenous methotrexate in mutant Nagase analbuminemic rats. Biopharm Drug Dispos 28:385-392.

Contreras V, Sepulveda P O, Shafer S L (2011) Bioavailability of propofol in humans. Int Soc Anaesth Pharmacol Annu Meet 21-23.

Cozanitis D A, Levonen K, Marvola M, Rosenberg P H, Sandholm M (1991) A comparative study of intravenous and rectal administration of propofol in piglets. Acta Anaesthesiol Scand 35:575-577.

DeBalli P (2003) The use of propofol as an antiemetic. Int Anesthesiol Clin 41:67-77.

Dong X P, Xu T L (2002) The actions of propofol on gamma-aminobutyric acid-A and glycine receptors in acutely dissociated spinal dorsal horn neurons of the rat. Anesth Analg 95:907-914 (table of contents).

Dutta S, Ebling W F (1997) Emulsion formulation reduces propofol's dose requirements and enhances safety. Anesthesiology 87:1394-1405.

Dutta S, Ebling W F (1998) Formulation-dependent brain and lung distribution kinetics of propofol in rats. Anesthesiology 89:678-685.

Fechner J, Ihmsen H, Hatterscheid D, Schiessl C, Vornov J J, Burak E (2003) Pharmacokinetics and clinical pharmacodynamics of the new propofol prodrug GPI 15715 in volunteers. Anesthesiology 99:303-313.

Garnock-Jones K P, Scott L J (2010) Fospropofol. Drugs 70:469-477.

Glen J B, Hunter S C, Blackburn T P, Wood P (1985) Interaction studies and other investigations of the pharmacology of propofol ('Diprivan'). Postgrad Med J 61(Suppl 3):7-14.

Hargreaves K, Dubner R, Brown F, Flores C, Joris J (1988) A new and sensitive method for measuring thermal nociception in cutaneous hyperalgesia. Pain 32:77-88.

Hiraoka H, Yamamoto K, Miyoshi S, Morita T, Nakamura K, Kadoi Y et al (2005) Kidneys contribute to the extrahepatic clearance of propofol in humans, but not lungs and brain. Br J Clin Pharmacol 60:176-182.

Hiraoka H, Yamamoto K, Okano N, Morita T, Goto F, Horiuchi R (2004) Changes in drug plasma concentrations of an extensively bound and highly extracted drug, propofol, in response to altered plasma binding. Clin Pharmacol Ther 75:324-330.

Jewett B A, Gibbs L M, Tarasiuk A, Kendig J J (1992) Propofol and barbiturate depression of spinal nociceptive neurotransmission. Anesthesiology 77:1148-1154.

Kam P C, Tan K H (1996) Pruritus—itching for a cause and relief? Anaesthesia 51:1133-1138.

Krusz J C, Scott V, Belanger J (2000) Intravenous propofol: unique effectiveness in treating intractable migraine. Headache 40:224-230.

Kurt M, Bilge S S, Kukula O, Celik S, Kesim Y (2003) Anxiolytic-like profile of propofol, a general anesthetic, in the plus-maze test in mice. Pol J Pharmacol 55:973-977.

Mahajan B, Kaushal S, Mahajan R (2012) Fospropofol. J Pharmacol Pharmacother 3:293-296.

Mahajan B, Kaushal S, Mahajan R (2012) Fospropofol: pharmacokinetics? J Anaesthesiol Clin Pharmacol 28:134-135.

Moghaddam M F, Bogdanffy M S, Brown A, Ford K, Shalaby L (2002) Plasma pharmacokinetics and tissue distribution of a N-pyrrolo-[1,2-c]imidazolylphenyl sulfonamide in rats. Drug Metab Dispos 30:47-54.

Mueller S W, Moore G D, MacLaren R (2010) Fospropofol disodium for procedural sedation: emerging evidence of its value? Clin Med Insights Ther 2:513-522.

Murugaiah K D, Hemmings H C Jr (1998) Effects of intravenous general anesthetics on [3H]GABA release from rat cortical synaptosomes. Anesthesiology 89:919-928.

Nishiyama T, Matsukawa T, Hanaoka K (2004) Intrathecal propofol has analgesic effects on inflammation-induced pain in rats. Can J Anaesth 51:899-904.

Orser B A, Wang L Y, Pennefather P S, MacDonald J F (1994) Propofol modulates activation and desensitization of GABAA receptors in cultured murine hippocampal neurons. J Neurosci 14:7747-7760.

Pain L, Oberling P, Launoy A, Di Scala G (1999) Effect of nonsedative doses of propofol on an innate anxiogenic situation in rats. Anesthesiology 90:191-196.

Plummer G F (1987) Improved method for the determination of propofol in blood by high-performance liquid chromatography with fluorescence detection. J Chromatogr 421:171-176.

Raoof A A, Augustijns P F, Verbeeck R K (1996) In vivo assessment of intestinal, hepatic, and pulmonary first pass metabolism of propofol in the rat. Pharm Res 13:891-895.

Ratnakumari L, Hemmings H C Jr (1997) Effects of propofol on sodium channel-dependent sodium influx and glutamate release in rat cerebrocortical synaptosomes. Anesthesiology 86:428-439.

Rossi H L, Neubert J K (2008) Effects of environmental enrichment on thermal sensitivity in an operant orofacial pain assay. Behav Brain Res 187:478-482.

Schywalsky M, Ihmsen H, Knoll R, Schwilden H (2005) Binding of propofol to human serum albumin. Arzneimittelforschung 55:303-306.

Schywalsky M, Ihmsen H, Tzabazis A, Fechner J, Burak E, Vornov J et al (2003) Pharmacokinetics and pharmacodynamics of the new propofol prodrug GPI 15715 in rats. Eur J Anaesthesiol 20:182-190.

Shah A, Mistry B, Gibiansky E, Gibiansky L (2008) Fospropofol assay issues and impact on pharmacokinetic and pharmacodynamic evaluation. Anesthesiology 109:937 (discussion 937).

Sheridan D C, Spiro D M, Nguyen T, Koch T K, Meckler G D (2012) Low-dose propofol for the abortive treatment of pediatric migraine in the emergency department. Pediatr Emerg Care 28:1293-1296.

Shimizu M, Yamakura T, Tobita T, Okamoto M, Ataka T, Fujihara H (2002) Propofol enhances GABA(A) receptor-mediated presynaptic inhibition in human spinal cord. NeuroReport 13:357-360.

Skrajnar S, Cerne M, Bozic M, Peternel L (2009) Effect of replacement fluids saline, gelofusine, and blood on biochemical and hematological parameters in rats subjected to repeated blood sampling. Med Sci Monit 15:BR293-BR300.

Soleimanpour H, Ghafouri R R, Taheraghdam A, Aghamohammadi D, Negargar S, Golzari S E et al (2012) Effectiveness of intravenous dexamethasone versus propofol for pain relief in the migraine headache: a prospective double blind randomized clinical trial. BMC Neurol 12:114.

Soleimanpour H, Taheraghdam A, Ghafouri R R, Taghizadieh A, Marjany K, Soleimanpour M (2012) Improvement of refractory migraine headache by propofol: case series. Int J Emerg Med 5:19.

Tall J M (2009) Housing supplementation decreases the magnitude of inflammation-induced nociception in rats. Behav Brain Res 197:230-233.

Tibbs G R, Rowley T J, Sanford R L, Herold K F, Proekt A, Hemmings H C Jr et al (2013) HCN1 channels as targets for anesthetic and nonanesthetic propofol analogs in the amelioration of mechanical and thermal hyperalgesia in a mouse model of neuropathic pain. J Pharmacol Exp Ther 345:363-373.

Tsagogiorgas C, Theisinger S, Holm P, Thiel M, Quintel M, Holm R (2013) Buccal absorption of propofol when dosed in 1-perfluorobutylpentane to anaesthetised and conscious Wistar rats and Gottingen mini-pigs. Eur J Pharm Biopharm 85:1310-1316.

Unlugenc H, Guler T, Gunes Y, Isik G (2004) Comparative study of the antiemetic efficacy of ondansetron, propofol and midazolam in the early postoperative period. Eur J Anaesthesiol 21:60-65.

Vasileiou I, Xanthos T, Koudouna E, Perrea D, Klonaris C, Katsargyris A et al (2009) Propofol: a review of its non-anaesthetic effects. Eur J Pharmacol 605:1-8.

Vornov J J, Wozniak K M, Wu Y, Rojas C, Rais R, Slusher B S (2013) Pharmacokinetics and pharmacodynamics of the glutamate carboxypeptidase II inhibitor 2-MPPA show prolonged alleviation of neuropathic pain through an indirect mechanism. J Pharmacol Exp Ther 346:406-413.

Welliver M, Rugari S M (2009) New drug, fospropofol disodium, a propofol prodrug. AANA J 77:301-308.

Xu A J, Duan S M, Zeng Y M (2004) Effects of intrathecal NMDA and AMPA receptors agonists or antagonists on antinociception of propofol. Acta Pharmacol Sin 25:9-14.

Zacny J P, Coalson D W, Young C J, Klafta J M, Lichtor J L, Rupani G et al (1996) Propofol at conscious sedation doses produces mild analgesia to cold pressor-induced pain in healthy volunteers. J Clin Anesth 8:469-474.

U.S. Pat. No. 6,969,508 for "Buccal, Polar and Non-Polar Spray or Capsule Containing Drugs for Treating Pain" to Dugger, III, issued Nov. 29, 2005.

U.S. Pat. No. 6,977,070 for "Buccal, Polar and Non-Polar Spray or Capsule Containing Drugs for Treating Disorders of the Central Nervous System" to Dugger, III, issued Dec. 20, 2005.

U.S. Patent Application Publication No. 20060222597 for "Buccal, Polar and Non-Polar Sprays Containing Propofol" to Dugger, III et al., published Oct. 5, 2006.

U.S. Patent Application Publication No. 20050002867 for "Buccal, Polar and Non-Polar Sprays Containing Propofol" to Dugger, III et al., published Jan. 6, 2005.

U.S. Patent Application Publication No. 20120289470 for "Transmucosal Administration of Drug Compositions for Treating and Preventing Disorders in Animals," to Heit et al., published Nov. 15, 2012.

U.S. Patent Application Publication No. 20060239928 for "Transmucosal Administration of Drug Compositions for Treating and Preventing Disorders in Animals," to Heit et al., published Oct. 26, 2006.

U.S. Patent Application Publication No. 20070202158 for "Methods of Administering Water-Soluble Prodrugs of Propofol for Extended Sedation," to Slusher et al., published Aug. 30, 2007.

U.S. Patent Application Publication No. 20080214508 for "Methods of Administering Water-Soluble Prodrugs of Propofol for Extended Sedation," to Slusher et al., published Sep. 4, 2008.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method for treating a condition selected from migraine, nausea, emesis, pain, pruritus, epilepsy, headache, and anxiety, the method comprising buccally, sublingually, or intranasally administering a prodrug of propofol, or a pharmaceutically acceptable salt thereof, to a subject in need of treatment thereof in an amount sufficient to deliver a therapeutically effective amount of propofol to the subject, wherein the prodrug of propofol is a compound of Formula (I):

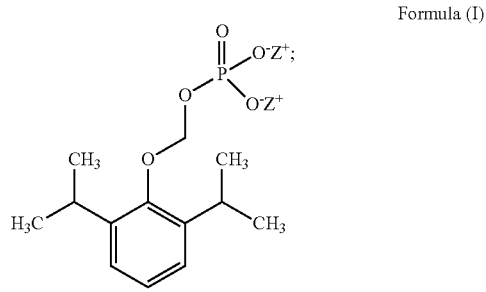

Formula (I)

wherein each Z is independently selected from the group consisting of hydrogen, an alkali metal, and an amine.

2. The method of claim 1, wherein the alkali metal is sodium.

3. The method of claim 1, wherein the compound of Formula (I), or pharmaceutically acceptable salt thereof, is administered intranasally in a form selected from the group consisting of a nasal spray, a nasal drop, a powder, a granule, a cachet, a tablet, an aerosol, a paste, a cream, a gel, an ointment, a salve, a foam, a paste, a lotion, a cream, an oil suspension, an emulsion, a solution, a patch, and a stick.

4. The method of claim 1, wherein the compound of Formula (I), or pharmaceutically acceptable salt thereof, is administered buccally in a form selected from the group consisting of a tablet, a capsule, a lozenge, a buccal spray, a mouth wash, a solution, a suspension, an emulsion, a powder, a granule, a thin film, and a gel.

5. The method of claim 1, wherein the compound of Formula (I), or pharmaceutically acceptable salt thereof, is administered sublingually in a form selected from the group consisting of a tablet, a capsule, a lozenge, a buccal spray, a mouth wash, a solution, a suspension, an emulsion, a powder, a granule, a thin film, and a gel.

6. The method of claim 1, wherein the method comprises administering the compound of Formula (I), or a pharmaceutically acceptable salt thereof, via a buccal, sublingual, or nasal spray composition.

7. The method of claim 6, wherein the buccal, sublingual, or nasal spray composition comprises a propellant.

8. The method of claim 7, wherein the propellant is selected from the group consisting of a hydrofluorocarbon, a linear or branched $C_3$ to $C_8$ hydrocarbon, and combinations thereof.

9. The method of claim 8, wherein the linear or branched $C_3$ to $C_8$ hydrocarbon is elected from the group consisting of propane, n-butane, iso-butane, n-pentane, iso-pentane, neo-pentane, and combinations thereof.

10. The method of claim 6, wherein the buccal, sublingual, or nasal spray composition comprises a polar solvent.

11. The method of claim 10, wherein the polar solvent is selected from the group consisting of water, linear or branched $C_2$ to $C_{18}$ alcohols, $C_2$ to $C_8$ polyalcohols, polyethyleneglycols, and combinations thereof.

12. The method of claim 6, wherein the buccal, sublingual, or nasal spray composition comprises an absorption or permeability enhancing agent.

13. The method of claim 12, wherein the absorption or permeability enhancing agent is selected from the group consisting of oleic acid, 23-lauryl ether, aprotinin, laurocapram, benzalkonium chloride, cetylpyridinium chloride, cetyltrimethylammonium bromide, cyclodextrin, dextran sulfate, lauric acid, lauric acid/propylene glycol, lysophosphatidylcholine, menthol, methoxysalicylate, methyloleate, phosphatidylcholine, polyoxyethylene, polysorbate 80, sodium EDTA (ethylenediamine tetraacetic acid), sodium glycocholate, sodium glycodeoxycholate, sodium lauryl sulfate, sodium salicylate, sodium taurocholate, sodium taurodeoxycholate, sulfoxides, an alkyl glycoside, and combinations thereof.

14. The method of claim 6, wherein the buccal, sublingual, or nasal spray composition further comprises an antioxidant.

15. The method of claim 14, wherein the antioxidant is selected from the group consisting of ascorbyl palmitate, alpha tocopherol, butylated hydroxyanisole, fumaric acid, and combinations thereof.

16. The method of claim 6, wherein the buccal, sublingual, or nasal spray composition further comprises a flavoring agent.

17. The method of claim 16, wherein the flavoring agent is selected from the group consisting of synthetic or natural oil of peppermint, one or more citrus oils, one of more fruit flavors, one or more sweeteners, and combinations thereof.

18. The method of claim 1, wherein the pain comprises neuropathic pain.

19. The method of claim 1, wherein the headache is a cluster headache.

20. A non-oral pharmaceutical composition for buccally, sublingually, or intranasally administering a prodrug of propofol, or a pharmaceutically acceptable salt thereof, to a subject in need of treatment thereof in an amount sufficient to deliver a therapeutically effective amount of propofol to the subject, wherein the prodrug of propofol is a compound of Formula (I):

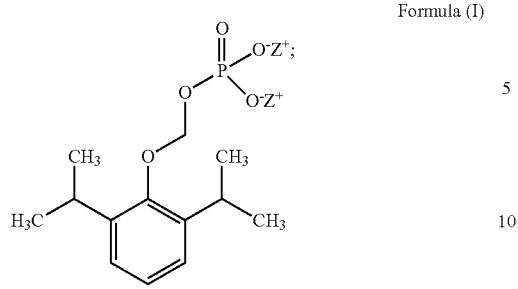
Formula (I)
wherein each Z is independently selected from the group consisting of hydrogen, an alkali metal, and an amine.
* * * * *